US011980380B2

(12) United States Patent
Friedman et al.

(10) Patent No.: US 11,980,380 B2
(45) Date of Patent: May 14, 2024

(54) CONTROLLABLE RETRIEVER WITH DISTAL CLOT ANCHOR

(71) Applicant: RAPID MEDICAL LTD., Yokneam (IL)

(72) Inventors: Aharon Friedman, Haifa (IL); Matan Gedulter, Givat Ela (IL); Moshe Miller, Jerusalem (IL)

(73) Assignee: RAPID MEDICAL LTD., Yokneam (IL)

( * ) Notice: Subject to any disclaimer, the term of this patent is extended or adjusted under 35 U.S.C. 154(b) by 62 days.

(21) Appl. No.: 16/470,366

(22) PCT Filed: Dec. 18, 2017

(86) PCT No.: PCT/IB2017/001773
§ 371 (c)(1),
(2) Date: Jun. 17, 2019

(87) PCT Pub. No.: WO2018/109566
PCT Pub. Date: Jun. 21, 2018

(65) Prior Publication Data
US 2019/0307471 A1    Oct. 10, 2019

Related U.S. Application Data

(60) Provisional application No. 62/435,796, filed on Dec. 18, 2016.

(51) Int. Cl.
*A61B 17/221*   (2006.01)
*A61F 2/01*   (2006.01)
(Continued)

(52) U.S. Cl.
CPC ............. *A61B 17/221* (2013.01); *A61F 2/01* (2013.01); *A61B 2017/00367* (2013.01);
(Continued)

(58) Field of Classification Search
CPC ........ A61B 17/221; A61B 2017/22034; A61B 2017/0042; A61B 2017/22072;
(Continued)

(56) References Cited

U.S. PATENT DOCUMENTS 8,715,314 B1* 5/2014 Janardhan ............. B23K 26/20
606/200
2002/0169474 A1   11/2002 Kusleika et al.
(Continued)

FOREIGN PATENT DOCUMENTS

CN      1269707 A    10/2000
CN    103841905 A     6/2014
(Continued)

OTHER PUBLICATIONS

WO 2011/032720 A1 Foriegn Translation , Mar. 2011.*
(Continued)

*Primary Examiner* — Ashley L Fishback
*Assistant Examiner* — Chima U Igboko
(74) *Attorney, Agent, or Firm* — FINNEGAN, HENDERSON, FARABOW, GARRETT & DUNNER LLP

(57) ABSTRACT

An intraluminal device may be provided including an elongated structure formed of a plurality of wires. The intraluminal device may include at least one expandable mesh segment configured to engage an obstruction in a body lumen, wherein the plurality of wires may be arranged into sets of looped wires that overlap to form the expandable mesh segment. The intraluminal device may also include at least one clot anchoring segment that may be configured to trap the obstruction to prevent downstream movement of the obstruction relative to the intraluminal device.

19 Claims, 15 Drawing Sheets

(51) Int. Cl.
   *A61B 17/00*   (2006.01)
   *A61B 17/22*   (2006.01)
(52) U.S. Cl.
   CPC ............ *A61B 2017/0042* (2013.01); *A61B 2017/22034* (2013.01); *A61B 2017/22072* (2013.01); *A61B 2017/22094* (2013.01); *A61F 2002/016* (2013.01); *A61F 2230/0026* (2013.01); *A61F 2230/0097* (2013.01); *A61F 2250/0023* (2013.01); *A61F 2250/0039* (2013.01)
(58) Field of Classification Search
   CPC . A61B 2017/22094; A61B 2017/00367; A61F 2/01; A61F 2/013; A61F 2250/0023; A61F 2250/0039; A61F 2230/0026; A61F 2230/0097; A61F 2002/016
   See application file for complete search history.

(56)  References Cited

U.S. PATENT DOCUMENTS

| | | | |
|---|---|---|---|
| 2009/0299393 A1 | 12/2009 | Martin et al. | |
| 2011/0213403 A1 | 9/2011 | Aboytes | |
| 2013/0030460 A1* | 1/2013 | Marks | A61B 17/221 606/200 |
| 2014/0128905 A1 | 5/2014 | Molaei | |
| 2014/0343663 A1* | 11/2014 | Sudin | A61B 17/12031 623/1.15 |
| 2017/0354402 A1 | 12/2017 | Lee et al. | |

FOREIGN PATENT DOCUMENTS

| | | | | |
|---|---|---|---|---|
| EP | 2713909 A1 * | 4/2014 | ............ | A61B 17/22 |
| GB | 2020557 A | 11/1979 | | |
| JP | S54-150888 A | 11/1979 | | |
| JP | 2015-504735 A | 2/2015 | | |
| WO | WO 2009/086482 A1 | 7/2009 | | |
| WO | WO-2011032720 A1 * | 3/2011 | ............ | A61F 2/90 |
| WO | WO 2011/106426 A1 | 9/2011 | | |
| WO | WO 2013/102848 A2 | 7/2013 | | |
| WO | WO 2016/071524 A1 | 5/2016 | | |
| WO | WO 2016/125018 A2 | 8/2016 | | |
| WO | WO 2017/077393 A1 | 5/2017 | | |

OTHER PUBLICATIONS

International Search Report for International Application No. PCT/IB2017/001773, dated Jul. 10, 2018 (2 pages).

Written Opinion of the International Searching Authority for International Application No. PCT/IB2017/001773, dated Jul. 10, 2018 (6 pages).

Extended European Search Report from the European Patent Office for counterpart European Application No. 17880659, dated Jun. 8, 2020 (8 pages).

First Office Action and Search Report dated Mar. 3, 2021, by the China National Intellectual Property Administration in counterpart Chinese Application No. 201780077640.4, with Translation (9 pages).

Office Action dated Oct. 1, 2021, from the Japan Patent Office in counterpart Japanese Patent Application No. 2019-531886, with Translation (7 pages).

Office Action dated Aug. 18, 2022, from the Japan Patent Office in counterpart Japanese Patent Application No. 2019-531886, with Translation (8 pages).

* cited by examiner

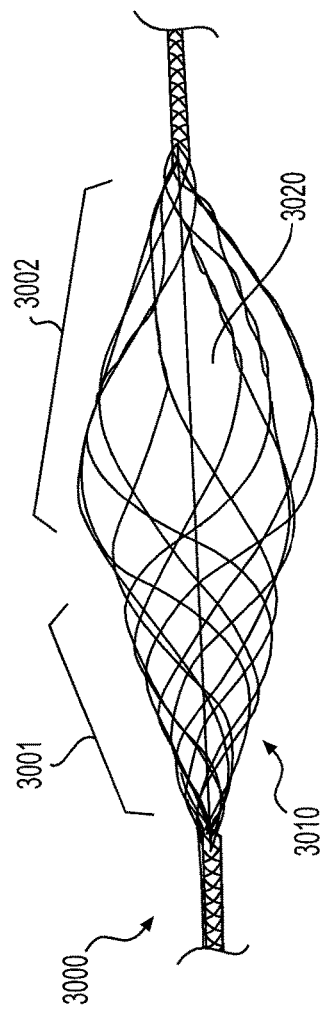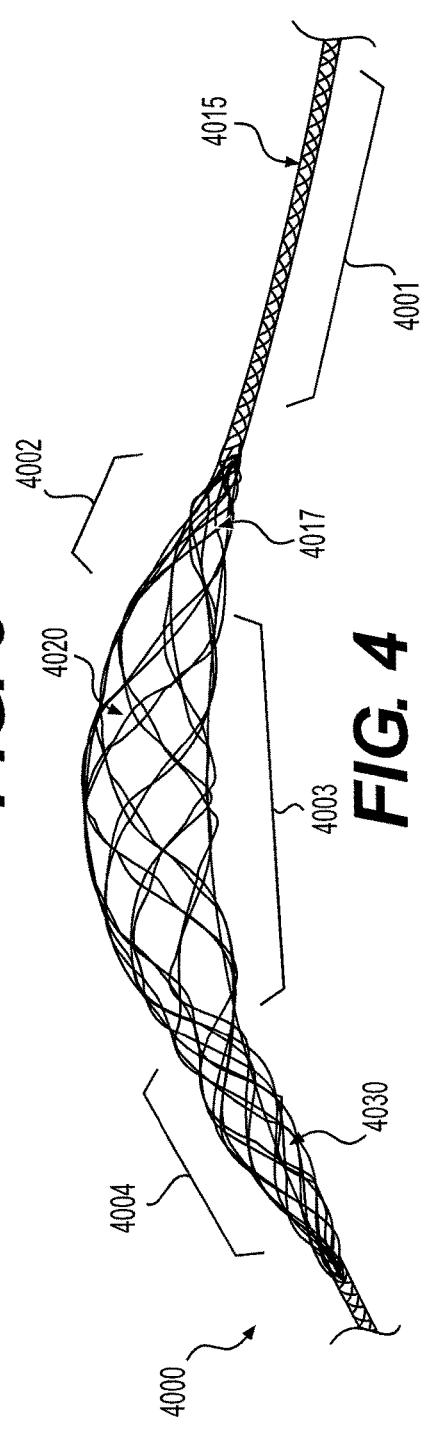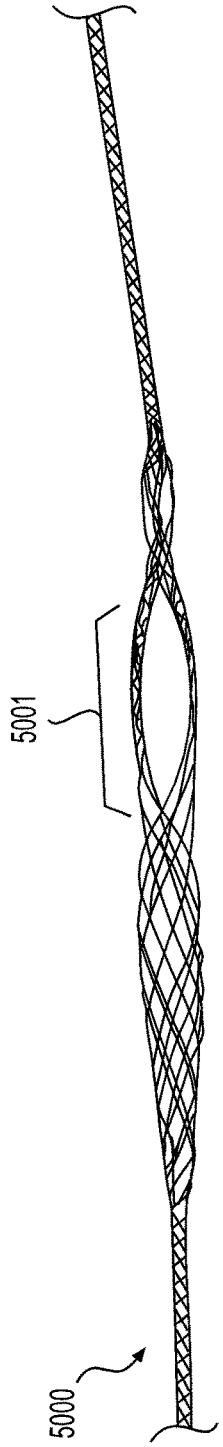

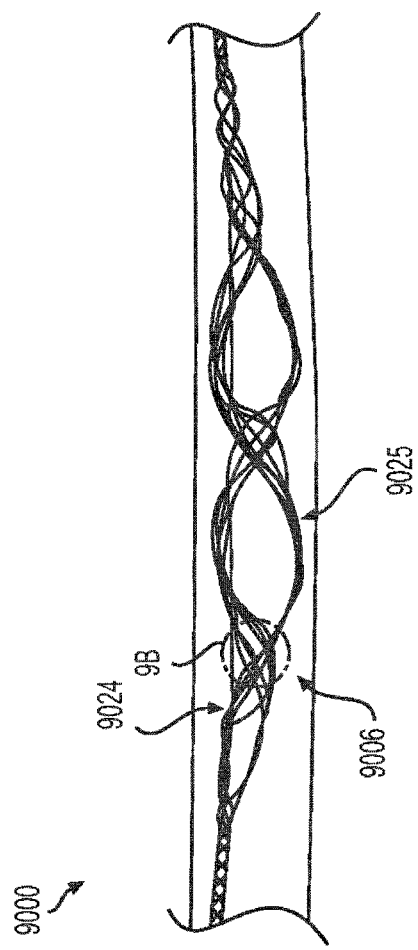
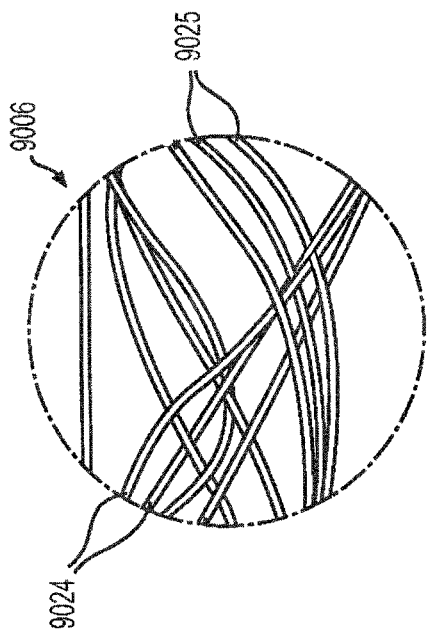
FIG. 9A
FIG. 9B
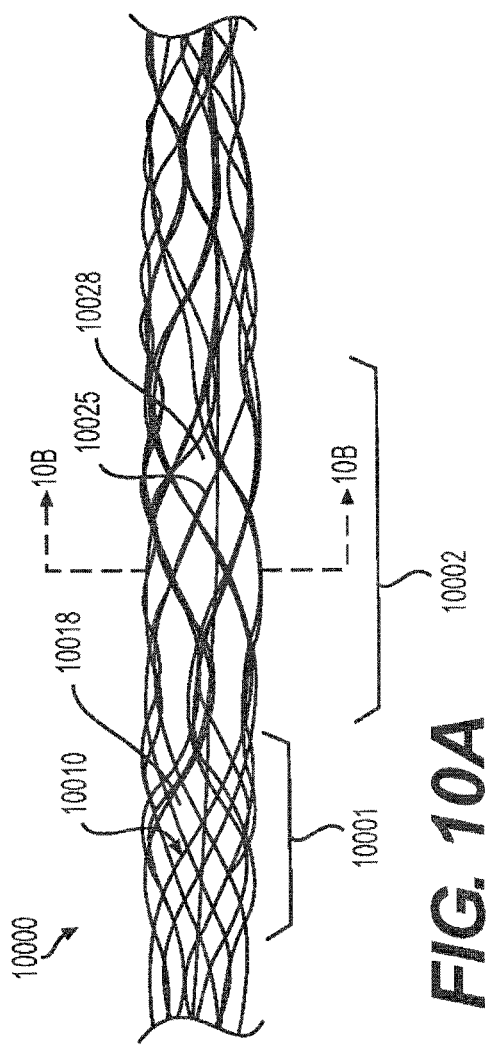
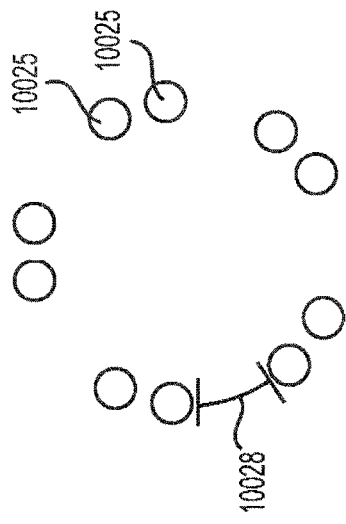
FIG. 10A
FIG. 10B

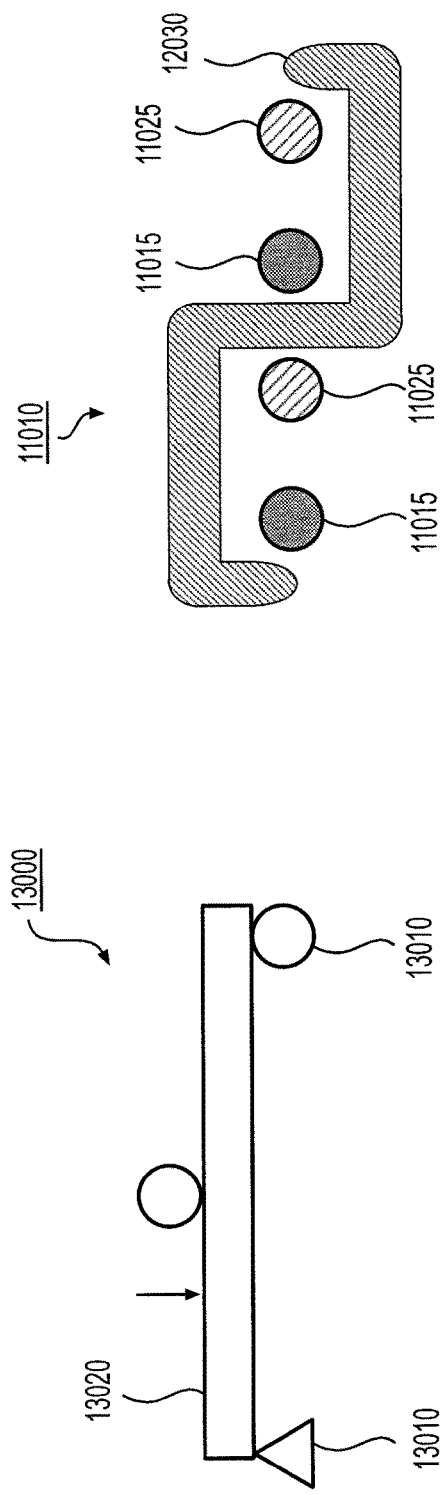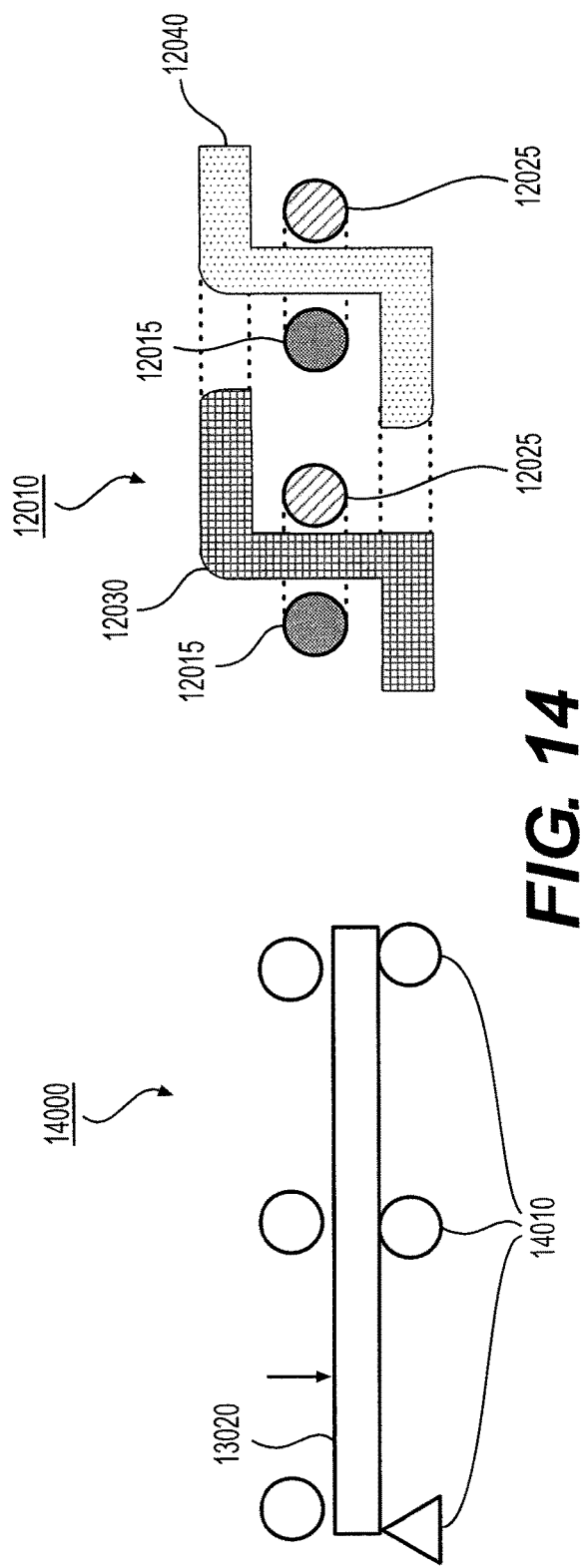

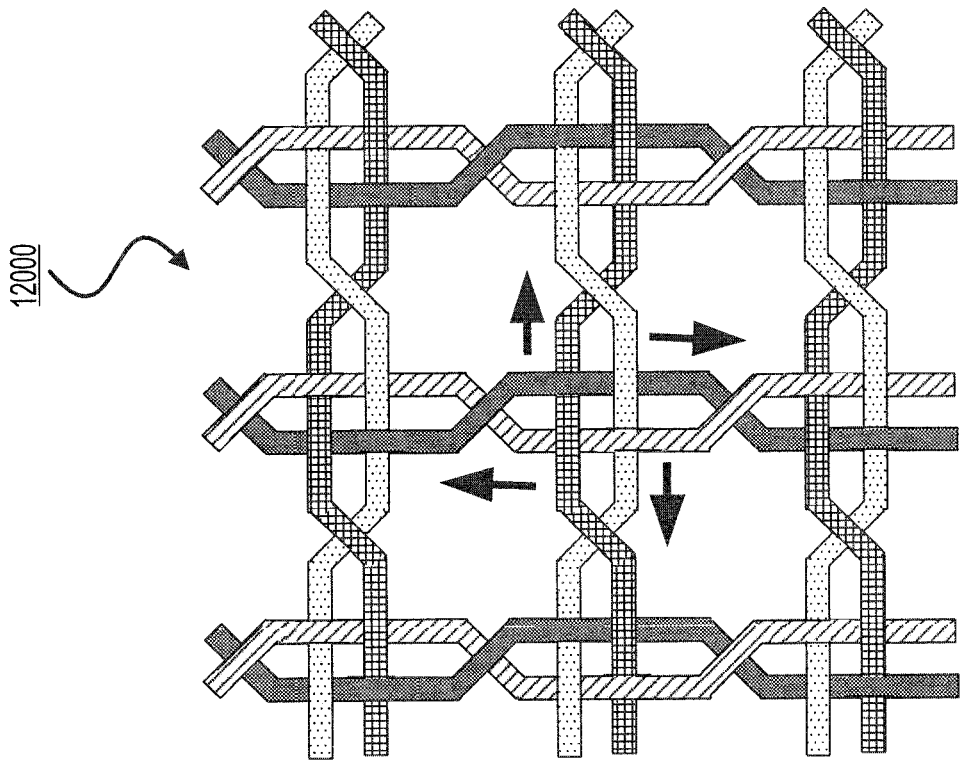
FIG. 19C
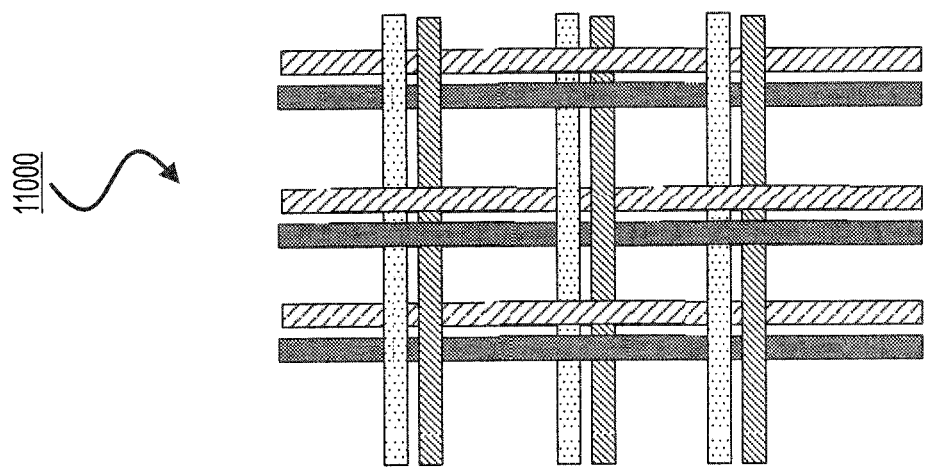

CONTROLLABLE RETRIEVER WITH DISTAL CLOT ANCHOR

PRIORITY

This application is a U.S. national stage entry under 35 U.S.C. § 371 of International Application No. PCT/162017/ 001773, filed Dec. 18, 2017, which claims the benefit of priority from U.S. Provisional Application No. 62/435,796, filed Dec. 18, 2016, both of which are herein incorporated by reference in their entireties.

FIELD

This disclosure relates to intravascular and/or intraluminal medical devices that are configured to retrieve an obstruction from human blood vessels. Obstructions to be retrieved can include clots and clot material.

SUMMARY

The disclosed embodiments may include an intraluminal device including an elongated structure formed of a plurality of wires. The intraluminal device may include a plurality of sets of looped wires longitudinally located at an intermediate area of the elongated structure. The plurality of sets may be spaced circumferentially about the structure and configured to cooperate with each other to form a plurality of clot entry openings. At least one grouping of woven wires may be longitudinally located adjacent the intermediate area and may be configured such that when an opening force is exerted on the elongated structure, the at least one grouping may provide structural support to hold open first interstices between the plurality of sets of looped wires. In response to the opening force, second interstices may be formed between wires in the at least one grouping of woven wires and the first interstices in the looped wire sets may be larger than the second interstices between wires in each of the at least one grouping.

In another embodiment, at least one grouping of the intraluminal device may include at least two groupings of woven wires, and each grouping may be spaced longitudinally from each other on opposite sides of the intermediate area containing the plurality of sets of looped wires. The at least two groupings of woven wires may cooperate with each other such that when an opening force is exerted on the wire structure, the at least two groupings provide structural support to hold open first interstices between the plurality of sets of looped wires. In response to the opening force, the second interstices may be formed between wires in each of the at least two groupings, and the first interstices in the looped wire sets may be larger than the second interstices between wires in each of the at least two groupings.

In another embodiment, the elongated structure of the intraluminal device may be formed of at least 8 wires, and each of the plurality of sets of looped wires may be formed of the same at least 8 wires as the at least one grouping of woven wires.

In another embodiment, the elongated structure of the intraluminal device may be formed of 12 wires that, in the intermediate area, may define six sets of looped wires. In the adjacent area, the 12 wires may collectively form the at least one grouping of woven wires. In another exemplary embodiment, each of the 12 wires may have a diameter of about 80 microns. In another exemplary embodiment, each wire of the intraluminal device may have a diameter of about 75 microns. By way of another example, each wire of the intraluminal device may have a diameter between 60 and 85 microns. In yet other examples the wires may be less than 60 microns and greater than 85 microns. In further examples, a single intraluminal device may have wires of varying diameters.

In another embodiment, an intraluminal device may include an elongated structure formed of a plurality of wires. The intraluminal device may include a first region wherein the plurality of wires may be twisted to form a shaft and a second region, adjacent to the first region, wherein the plurality of wires may be woven to form a scaffold. The intraluminal device may also include a third region, adjacent to the second region, wherein the plurality of wires may be separated into sets of looped pairs to form a clot capture structure. The intraluminal device may also include a fourth region wherein the plurality of wires may be braided to form a dense filter configured to catch a blood clot.

In another embodiment, the elongated structure of the intraluminal device may be configured to transition between a collapsed position for delivery to a treatment site, and an expanded position in response to an opening force exerted thereon.

In another embodiment, the elongated structure of the intraluminal device may be configured such that, for example, when the opening force is applied, first interstices may be formed between wires in the second region, and second interstices may be formed between wires in the third region, such that the second interstices are larger than the first interstices.

In another embodiment, the elongated structure of the intraluminal device may be configured such that, for example, when the opening force is applied, third interstices are formed between wires in the fourth region, such that, for example, the third interstices are smaller than both the first interstices and the second interstices.

In another embodiment, the intraluminal device may include a fifth region, adjacent to the fourth region, and wherein the plurality of wires in the fifth region may be twisted to form an additional shaft. In another embodiment, the intraluminal device may include 12 wires and each wire may have a diameter of about 80 microns. In one embodiment, for example, each wire of the intraluminal device may have a diameter of about 75 microns. By way of another example, each wire of the intraluminal device may have a diameter between 60 and 85 microns.

In another embodiment, the elongated structure of the intraluminal device may be configured such that the opening force may be applied through axial movement of the first region. In yet another embodiment, the intraluminal device may include an additional second region of scaffold between the third region and the fourth region.

In another embodiment, an intraluminal device may include an elongated structure formed of a plurality of wires and the device may also include a plurality of cables each formed of a subset of the plurality of wires. The pairs of cables may cross each other at a plurality of intersection locations and at the plurality of intersection locations, wires from each pair of crossing cables may be unwound and woven together with wires from a paired crossing cable. Further, the wires of the crossing cables may be woven together at the intersection locations in a manner permitting the woven-together wires to move relative to each other when an opening force is applied to the elongated structure. Also, in response to the opening force exerted thereon, at the intersection locations, pairs of crossing cables may be configured to pivot relative to each other as the elongated structure transitions between a collapsed position for delivery to a treatment site, and an expanded clot capture position.

In another embodiment, the elongated structure of the intraluminal device may include an elongated structure formed of a plurality of wires, the intraluminal device including a first region wherein the plurality of wires are twisted to form a shaft. The intraluminal device may also include a second region, adjacent to the first region, wherein the plurality of wires are woven to form a scaffold. The intraluminal device may also include a third region, wherein the plurality of wires are separated into sets of looped pairs to form at least one clot engaging expandable mesh segment. The intraluminal device may also include a fourth region, including at least one clot anchoring segment.

In at least some embodiments, the at least one clot anchoring segment of the intraluminal device may be adjustable to form a platform, and the expansion of the at least one clot anchoring segment is controlled by a control wire together with the at least one clot engaging expandable mesh segment.

In at least some embodiments, the at least one clot anchoring segment may self-expand and a control wire may be connected to a distal end of the at least one clot engaging expandable mesh segment.

In at least some embodiments, the device may have a first control wire and a second control wire, and the first control wire may control expansion of the at least one clot engaging expandable mesh segment and the second control wire may control expansion of the at least one clot anchoring segment.

In at least some embodiments, the at least one clot engaging expandable mesh segment may include large pores and may be self-expanded or controllably adjusted to open while applying radial force to penetrate and contain the clot.

In at least some embodiments, the at least one clot anchoring segment may be expanded to form a platform which is configured to engage a clot and push it upstream.

In at least some embodiments, the at least one clot anchoring segment may include two adjustable clot anchoring segments. The two adjustable clot anchoring segments may be expanded by a single control wire that is connected a distal end of the two adjustable clot anchoring segments. The two adjustable clot anchoring segments may also be expanded by separate control wires.

In at least some embodiments, the at least one clot engaging expandable mesh segment includes two clot engaging expandable mesh segments.

BRIEF DESCRIPTION OF THE DRAWINGS

The accompanying drawings, which are incorporated in and constitute a part of this specification, illustrate disclosed embodiments and, together with the description, serve to explain the disclosed embodiments.

FIG. 3 is an illustration of a third exemplary intraluminal device in accordance with at least one of the disclosed embodiments;

FIG. 4 is an illustration of a fourth exemplary intraluminal device in accordance with at least one of the disclosed embodiments;

FIG. 5 is an illustration of a fifth exemplary intraluminal device in accordance with at least one of the disclosed embodiments;

FIG. 9A is an illustration of another exemplary intraluminal device in accordance with at least one of the disclosed embodiments;

FIG. 9B is an enlarged view of a portion of the exemplary intraluminal device shown in FIG. 9A;

FIG. 10A is an illustration of another exemplary intraluminal device in accordance with at least one of the disclosed embodiments;

FIG. 10B is a cross-sectional view of a portion of the exemplary intraluminal device shown in FIG. 10A;

FIG. 13 is a cross section view of an exemplary braided structure without twists, and an associated loaded beam diagram;

FIG. 14 is a cross section view of an exemplary braided structure with twists, and an associated loaded beam diagram;

FIGS. 19A-C illustrate a number of braiding structures consistent with at least some of the disclosed embodiments;

Annotations appearing in the figures are exemplary only, and are not restrictive of the invention as claimed.

DETAILED DESCRIPTION

Reference will now be made in detail to the present embodiments (exemplary embodiments) of the disclosure, examples of which are illustrated in the accompanying drawings. Wherever possible, the same reference numbers will be used throughout the drawings to refer to the same or like parts.

Figure 1:
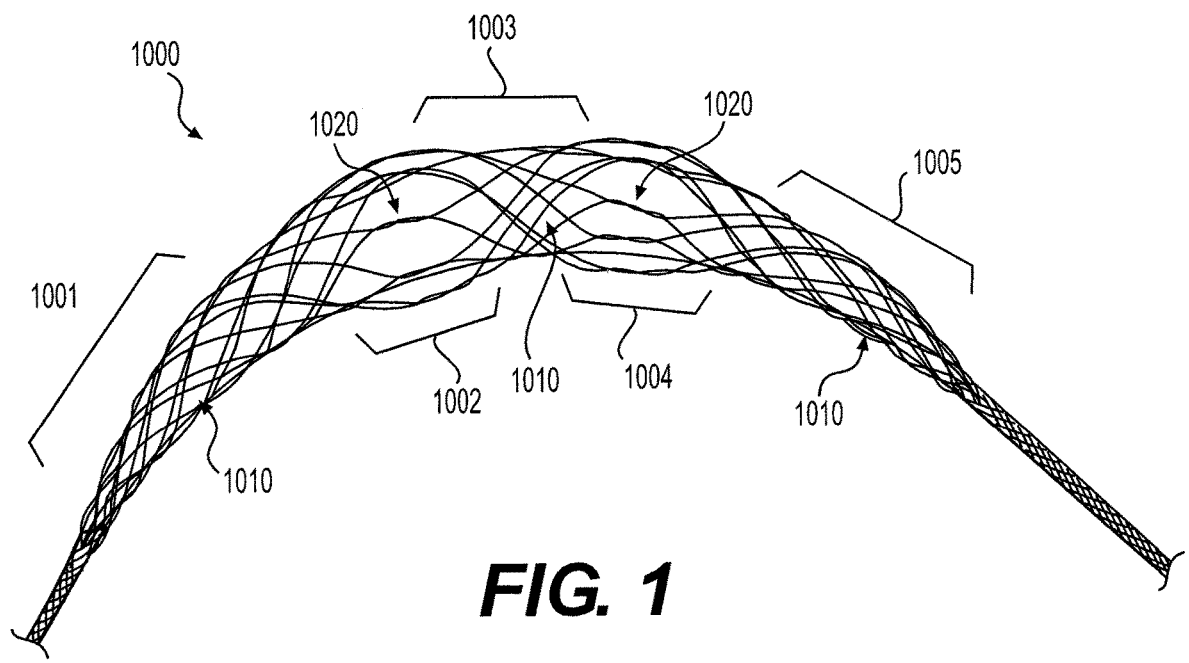
FIG. 1 is an illustration of a first exemplary intraluminal device, consistent with at least one of the disclosed embodiments.

FIG. 1 illustrates an exemplary intraluminal device 1000 including five alternating wire zones 1001, 1002, 1003, 1004, and 1005. Zones 1001, 1003 and 1005 include groups of woven wires 1010 and may provide structural support for zones 1002 and 1004. Additionally, since the openings between wires 1010 of zone 1 and 5 may be much smaller they also may provide a distal and proximal filter. (An example of variable sized openings is illustrated in FIGS. 10A-B, discussed below.) As a result, clot particles that might appear during the retrieval may be captured at these zones, for example. As further shown in FIG. 1, zones 1002 and 1004 may be constructed of looped wires 1020 to allow a large clot capturing area. And also shown in FIG. 1, zones 1001, 1003, and 1005 may be constructed by woven wires 1010. The number of zones illustrated are exemplary. More or less zones may be provided.

Figure 2:
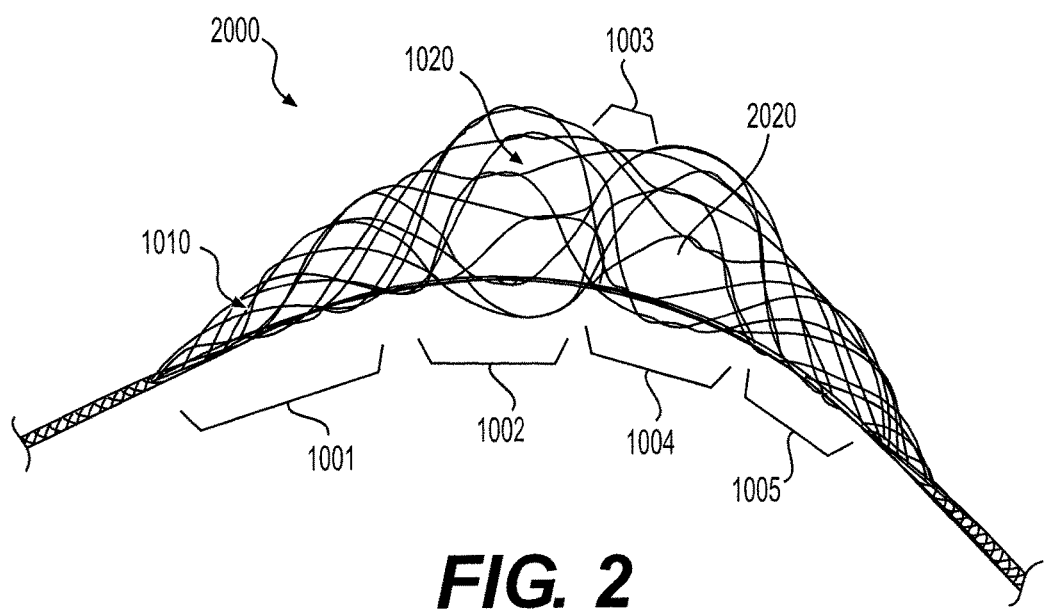
FIG. 2 is an illustration of a second exemplary intraluminal device in accordance with at least one of the disclosed embodiments.

FIG. 2 illustrates an intraluminal device 2000 in a more open position than illustrated in FIG. 1, highlighting the clot entry cells 2020 that may be made from the looped wires 1020. As further shown in FIG. 2, zones 1002 and 1004 may be constructed of looped wires 1020 to allow a large clot capturing area.

FIG. 3 illustrates yet another exemplary intraluminal device 3000. In this example, as shown in FIG. 3, the device 3000 may be configured so as to include only two different zones. Zone 3001 may be constructed from a group of woven wires 3010, such as for example, densely braided, which provides structural support for the device 3000. In addition, zone 3001 may also serve as a distal filter that prevents emboli from the distal vasculature. As also shown in FIG. 3, zone 3002 may be constructed from wires which are looped which are longitudinally located and provide the clot entry zone 3020. Additionally, zone 3001 may, for example, give structural support and may also serve as a distal filter. As further shown in FIG. 3, zone 3002 may be the clot entering zone.

FIG. 4 illustrates yet another exemplary intraluminal device 4000 with four regions. In the first region 4001, the wires may be twisted or coiled to form a shaft 4015. In the second region 4002, the wires may be woven to from a scaffold 4017 that supports the opening of the third region 4003. In the third region 4003, the wires may be woven set in looped pairs to form a clot capture structure 4020. For example, the wires of the third region 4003 may be loosely looped or loosely coupled. Further, the fourth region 4004 may be woven to form a distal filter 4030 that captures distal emboli or clot particles. The fourth region 4004 may also serve as a scaffold for the third region 4003.

FIG. 5 illustrates yet another exemplary intraluminal device 5000. For example, as shown in FIG. 5, the clot opening region 5001 may be woven from three wires that are looped together. Further, the number of wires that are looped together may be greater than two.

Figure 6:
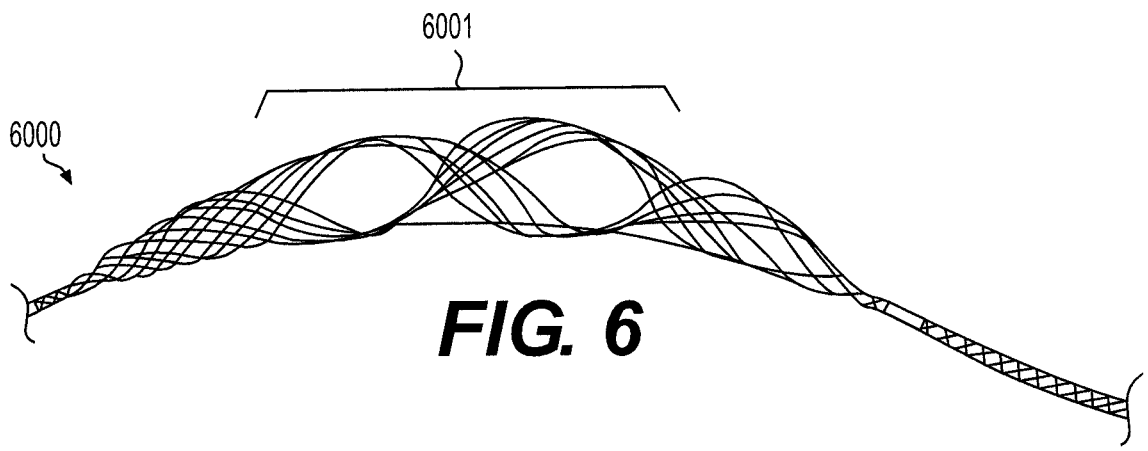
FIG. 6 is an illustration of a sixth exemplary intraluminal device in accordance with at least one of the disclosed embodiments.

FIG. 6 is illustrates yet another exemplary intraluminal device 6000. For example, as shown in FIG. 6, the clot opening region 6001 may be woven from three wires that are loosely looped together. Further, the number of wires that are looped together may be greater than two.

Figure 7:
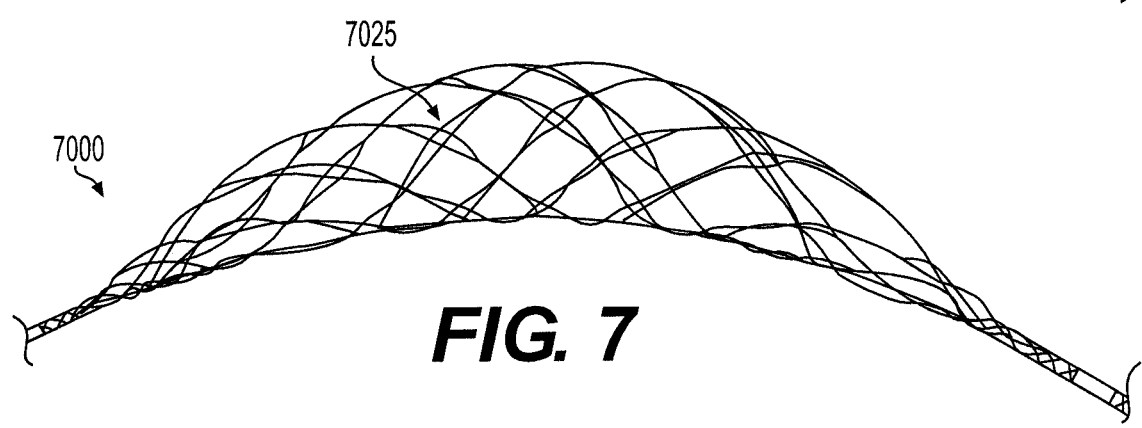
FIG. 7 is an illustration of a seventh exemplary intraluminal device in accordance with at least one of the disclosed embodiments.

FIG. 7 illustrates yet another exemplary intraluminal device 7000. For example, as shown in FIG. 7, the device 7000 may include six cables 7025, in which each cable 7025 may include paired wires. This may create a strong but flexible crossing. And this may further allow, for example, the device 7000 to achieve a flexible structure with a high radial force.

Figure 8:
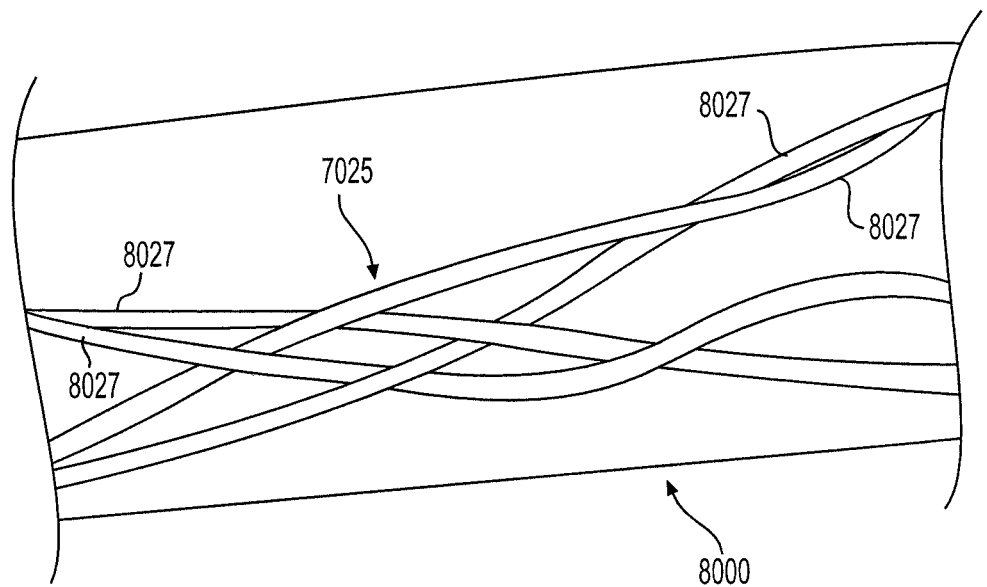
FIG. 8 is an illustration of exemplary cable interweaving, such as is disclosed in connection with FIG. 7.

FIG. 8 illustrates an example of cable interweaving 8000, as discussed above. Each cable 7025, for example, may be made from a looped pair of wires 8027 that are woven with a pair of wires 8027 from a crossing cable. As a result, for example, a semi-flexible and strong crossing point may be achieved.

FIGS. 9A-9B illustrate yet another exemplary intraluminal device. As shown in FIG. 9A, the cables, for example, may be made from three wires that are unwound and then woven together with the wires from the crossing cable. FIG. 9B also illustrates the cable crossing point 9006 where the cables (which includes wires 9024 and 9025) are unwound and woven back together. As discussed below in connection with FIGS. 12 and 19, the braiding structure of FIG. 9A may include a 12-wire braiding structure with a twist before and after each junction frame.

As discussed above in connection with FIG. 1, FIG. 10A illustrates device 10000 with variable-sized openings. Region 10001 includes groups of woven wires 10010 adjacent to intermediate location 10002, and may provide structural support for intermediate location 10002. Specifically, the groupings of woven wires 10010 in region 10001 can provide the support to hold open the first interstices 10028. The first interstices 10028 are larger than the second interstices 10018, where the second interstices are present in region 10001. The cross section illustrated in FIG. 10B depicts how the cables 10025 are circumferentially displaced in the intermediate location 10002. Cables 10025 are generally circumferentially displaced about a central region. Moreover, first interstices 10028 may provide relatively large openings for clot entry in the intermediate location 10002.

In accordance with embodiments consistent with the present disclosure, the exemplary intraluminal device may include, for example, two braiding mechanisms, configurations, or structures which may help increase the performance of the device relative to a device incorporating standard braiding structures.

Figure 12:
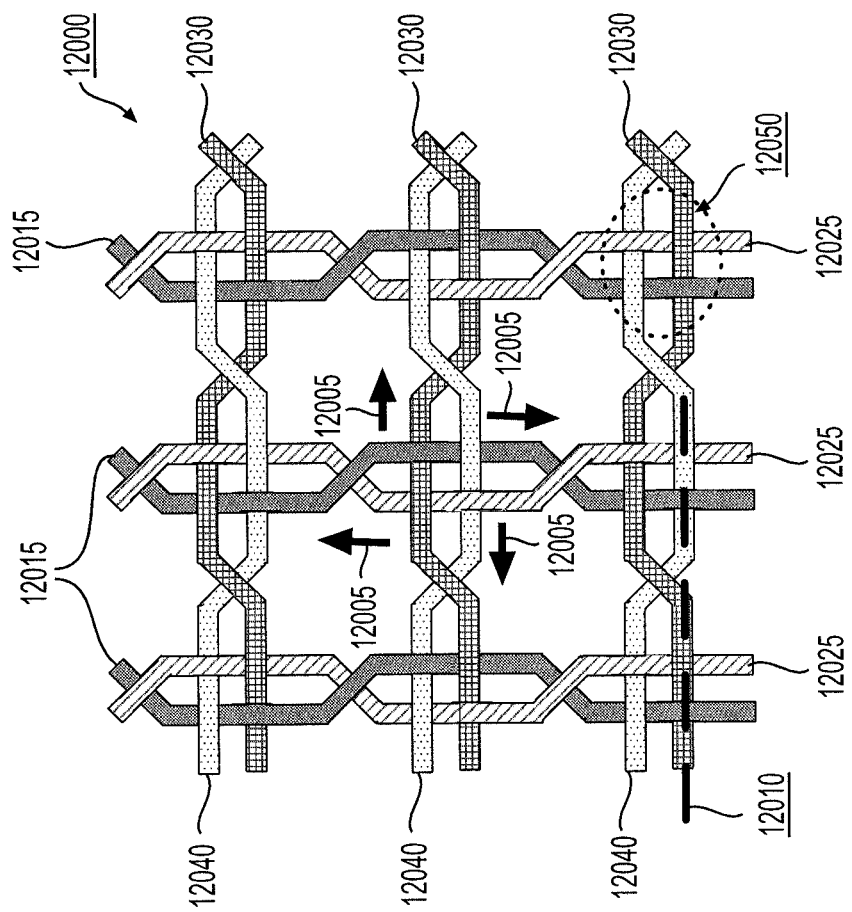
FIG. 12 is an illustration of a braid structure of an exemplary intraluminal device in accordance with at least one of the disclosed embodiments.
Figure 11:
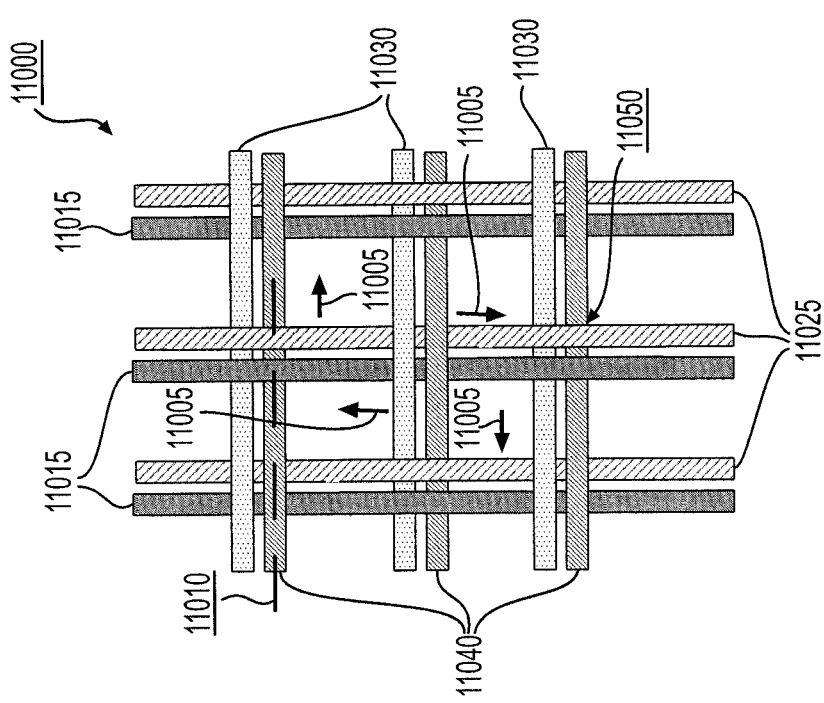
FIG. 11 is an illustration of a braid structure of an exemplary intraluminal device.

For example, as shown in FIG. 12, in accordance with at least some embodiments of an intraluminal device consistent with the present disclosure, the braiding structure 12000 may include a twist of wires before and after each junction frame 12050. Braiding structure 12000 includes three strands of two-wire pairs (two wires 12015 and 12025) braided with three stands of two-wire pairs (two wires 12030 and 12040). FIG. 12 depicts a total of nine (9) junction frames. The junction position within the mesh structure may help prevent slipping of wires across the twist which may otherwise work to become homogeneously separated on a circumference of a mesh structure of an intraluminal device. While a braid structure 11000, as shown in FIG. 11, may enable slippage (illustrated by arrows 11005) until the wire 11040 (for example) reaches a parallel wire 11030, the twists as shown in braiding structure 12000 shown in FIG. 12, may operate to help prohibit substantial slippage across the twist and enable a solid structure when the intraluminal device is expanded.

In accordance with at least some embodiments of an intraluminal device consistent with the present disclosure, and as illustrated in FIGS. 13 and 14, a braiding structure which includes a twist structure may add strength to a mesh structure by operating as a restraint system grasping the wire and dividing an external force applied on the mesh onto additional elements. FIG. 13 depicts cross section 11010 of braiding structure 11000 of FIG. 11 and FIG. 14 depicts cross section 12010 of braiding structure 12000 of FIG. 12. The dotted lines in cross section 12010 of FIG. 14 illustrate a twist in wires 12015 and 12025, and also illustrate a twist in wires 12030 and 12040. The force distribution mechanism in the braiding structures is similar, for example, to force distribution of a loaded beam with varying numbers of supports. This is also illustrated in FIGS. 13 and 14 with the loaded beam diagram 13000 (associated with braided structure 11000) and loaded beam diagram 14000 (associated with braided structure 12000). As illustrated in FIGS. 13 and 14, a loaded beam 13020 with three supports 14010, for example, will react to and distribute the force more effectively than a loaded beam 13020 with two supports 13010, as there is a smaller distance between three supports 14010.

In accordance with at least some embodiments consistent with the present disclosure, the exemplary intraluminal device may be delivered through a microcatheter with an internal diameter of between 0.013 inches and 0.027 inches. In some embodiments, the microcatheter may have an internal diameter of 0.017 inches. As a result, the exemplary intraluminal device may have a low profile (in a retracted or compressed state) that is less than that of the internal diameter of a microcatheter. In accordance with at least some embodiments of an intraluminal device consistent with the present disclosure, the device may have the five following parts, for example:
a) a control handle;
b) a stiff proximal shaft (for example, a stainless steel hypotube);
c) a flexible shaft (made from a cable of wires, for example);
d) an expandable mesh which is made from the same wires of the cable; and
e) a corewire/control wire which may be connected to the distal tip of the mesh and runs through the shafts to the handle.

Figure 19A:
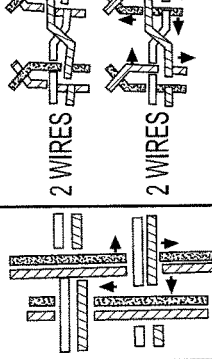

For example, as illustrated in the 8-wire row in FIG. 19A, an intraluminal device may include a flexible shaft with eight (8) wires (each wire having a diameter of 70 μm) and a mesh including eight (8) wires (each wire having a diameter of 70 μm). The eight wires, for example, may be formed, for example, by creating four strands of wires braided together, with each strand including two (2) wires each. As shown in FIG. 19A, and discussed above, the braiding structure of the intraluminal device may include a twist of wires before and after each junction frame to help prevent slippage. A detailed view of cable interweaving 8000 (discussed in connection with FIG. 8) is also shown in FIG. 19A. Cable interweaving 8000 illustrates a junction in the braiding structure of the intraluminal device in detail. The wires may, for example, be made from Nitinol. FIG. 19A also depicts a braiding structure of the intraluminal device without a twist before and after a junction frame.

In another exemplary embodiment, as illustrated in the 12-wire row in FIG. 19A, the intraluminal device may include a flexible shaft with twelve (12) wires and a mesh including twelve (12) wires. FIG. 19C depicts a detailed view of the 12-wire row in FIG. 19A. The twelve (12) wires may be formed, for example, by creating six strands of wires braided together: with three strands including two (2) wires each; while the other three strands may include two (2) wires each. As shown in FIG. 19C, and as discussed above (such as in connection with FIG. 8, which shows cable interweaving 8000, and FIG. 12, which shows braiding structure 12000), the braiding structure 12000 for this embodiment may include a twist of wires before and after each junction frame to help prevent slippage. FIG. 19C also depicts braiding structure 11000 without a twist before and after a junction frame. An exemplary intraluminal device with twelve (12) wires includes device 9000 of FIG. 9.

Figure 15:
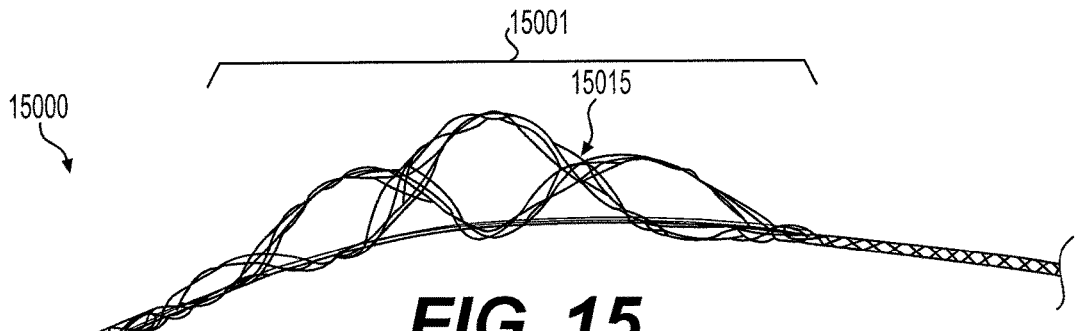
FIG. 15 is an illustration of an exemplary intraluminal device, consistent with at least one of the disclosed embodiments.
Figure 19B:
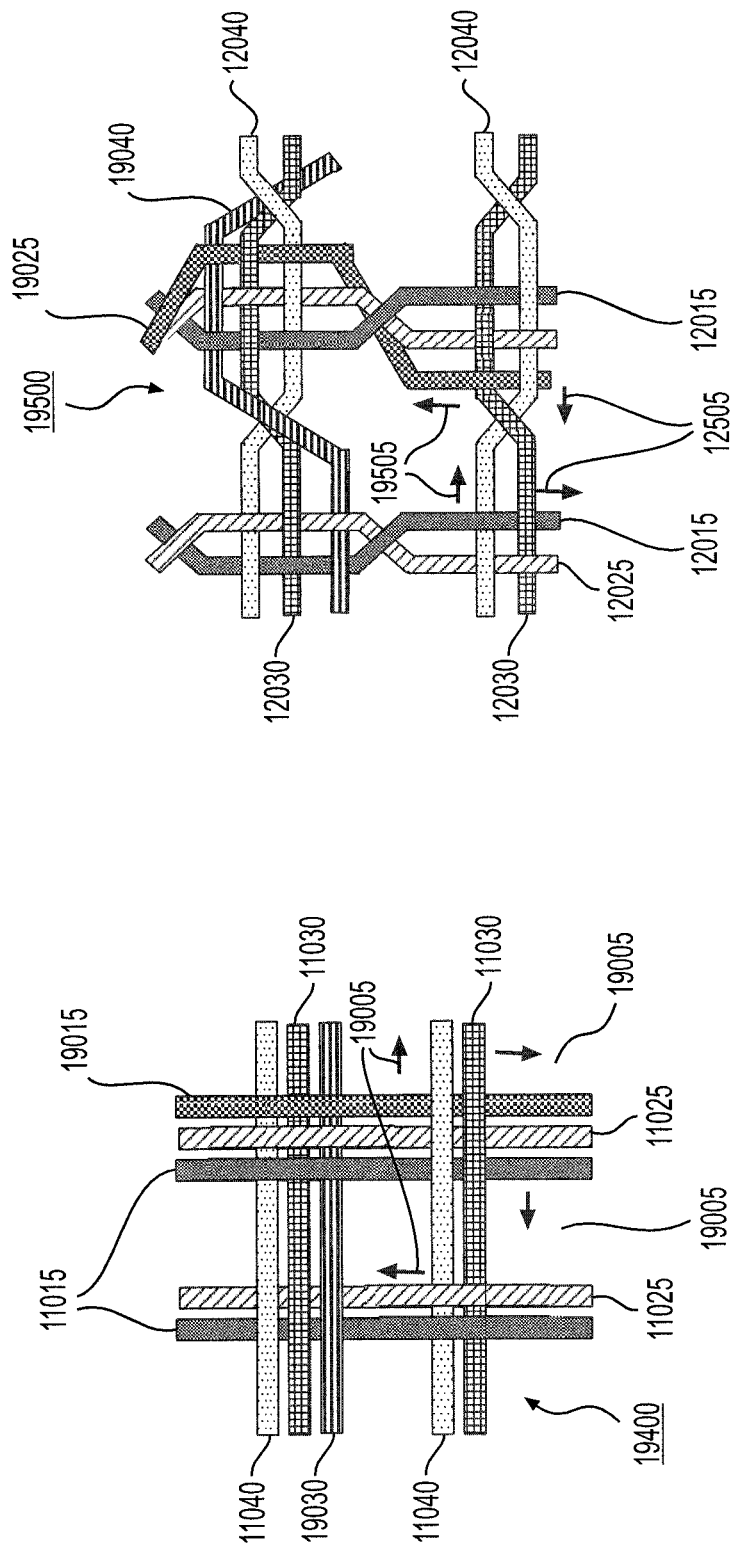

In accordance with another embodiment consistent with the present disclosure, as illustrated in the 10-wire row in FIG. 19, the flexible shaft of the exemplary intraluminal device may include a flexible shaft with ten (10) wires and a mesh including ten (10) wires. FIG. 19B depicts a detailed view of the 10-wire row in FIG. 19A. The ten (10) wires may be formed, for example, by creating four strands of wires braided together: with two strands including three (3) wires each; while the other two strands may include two (2) wires each. Exemplary braiding structures with ten (10) wires are illustrated in FIG. 19B. The braiding structure 19500 may include a twist of wires before and after each junction frame. Braiding structure 19500 includes two-wire strand (wires 12015 and 12025) and three-wire strand (wires 12015, 12025, and 19025) braided with two-wire strand (wires 12030 and 12040) and three-wire strand (12030, 12040, and 19040). Slippage arrows 19505 are also shown. A braiding structure 19400 without a twist is also illustrated. Braiding structure 19400 includes two-wire strand (wires 11015 and 11025) and three-wire strand (wires 11015, 11025, and 19015) braided with two-wire strand (wires 11030 and 11040) and three-wire strand (11030, 11040, and 19030). Slippage arrows 19005 are also shown. In each strand of wires, the wires may, for example, be intertwined to create a stable strand. The wires may, for example, be made from Nitinol, and this configuration may be achieved, for example, by cutting two wires at a transition between a cable and mesh (although this may involve another manufacturing step). As shown in FIG. 15, which represents a general view of an exemplary intraluminal device 15000 in accordance with the present disclosure, the strands may cross each other to create large openings (cells). In the intersections, for example, the strands may be intertwined with one another to create a loosely coupled junction. Before and after the junction, for example, the wires of the strands may be intertwined.

Figure 16:
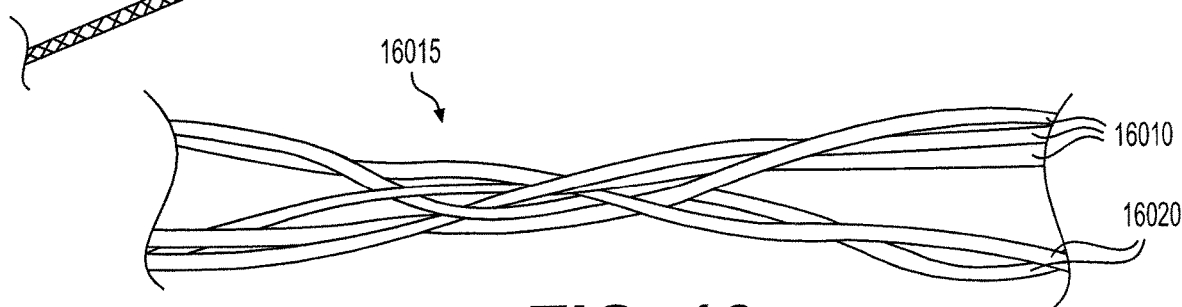
FIG. 16 is an enlarged view of a portion of the exemplary intraluminal device shown in FIG. 15.
Figure 17:
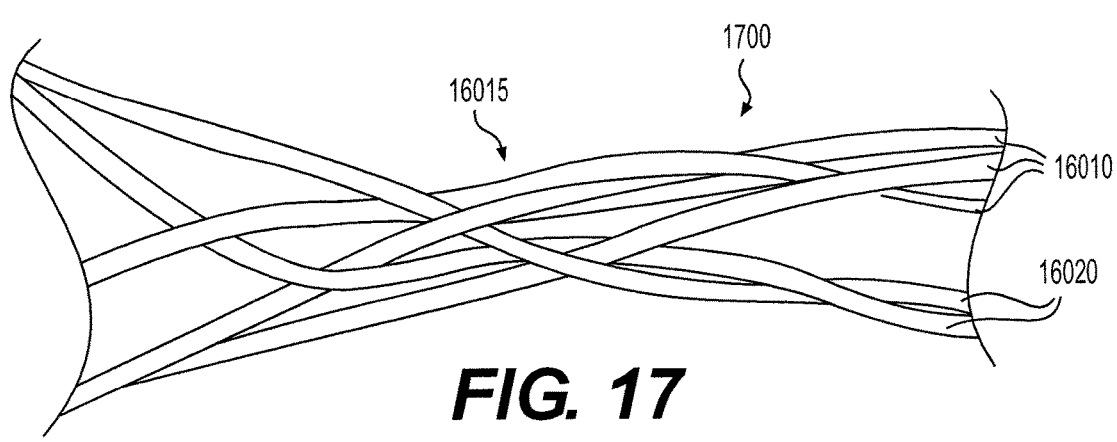
FIG. 17 is an enlarged view of a portion of the exemplary intraluminal device shown in FIG. 15 in an expanded position.
Figure 18:
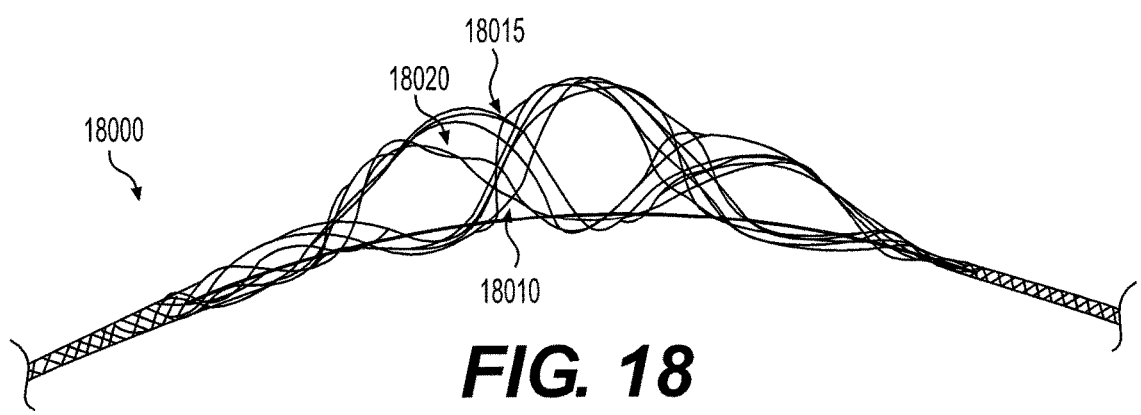
FIG. 18 is an illustration of exemplary intraluminal device in an expanded position in accordance with at least one of the disclosed embodiments.

As shown in FIG. 16, a strand of two wires (i.e., wires 16020) may cross a strand of three wires (i.e., wires 16010). The intertwined wires before and after the junction and the intertwining of the wires inside the junction may create a loosely coupled but stable junction and cross-section, which helps prevent slippage and create large cells, ultimately helping to resist collapse of the device when expanded with high radial force within a tube. And, as shown in FIGS. 17-18 (where FIG. 17 is a detail of region 16015 of FIG. 16 in an expanded configuration, and FIG. 18 is a detail of FIG. 15 in an expanded configuration), when the mesh is expanded, the junction structure keeps the wires together even when the mesh is expanded. As a result, the mesh size remains the same.

FIGS. 19A-C illustrate 8-, 10-, and 12-wire junctions and configurations. In addition, as discussed above, devices 15000 and 18000, and the detailed views of FIGS. 16 and 17 may use the 12-wire junctions of FIGS. 19A and 19C. Of course, these are only examples, and the wire junctions and configurations with more or less wires may be used, and that regardless of the number of wires, differing braiding arrangements may be employed.

Figure 20:
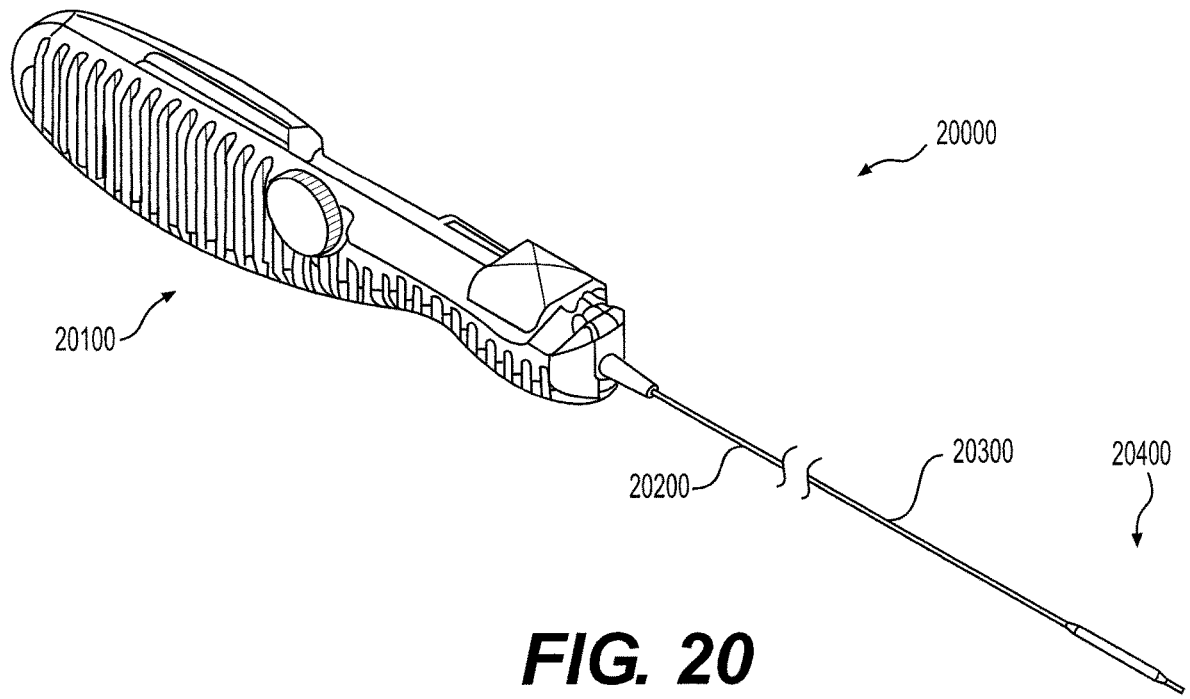
FIG. 20 is an illustration of another exemplary intraluminal device in accordance with at least one of the disclosed embodiments.

As shown in FIG. 20, in accordance with at least some alternative embodiments of an intraluminal device 20000 in accordance with the present disclosure, the device 20000 may have the five following parts, for example:
a) a control handle 20100;
b) a stiff proximal shaft 20200, such as a stainless steel hypotube;
c) a flexible shaft 20300 (made from a cable of wires, for example);
d) clot engaging component 20400, such as an clot engaging expandable mesh and/or an clot anchor platform which is made from the same wires of the cable of flexible shaft 20300; and
e) a corewire or control wire (not shown in FIG. 20) which may be connected to the distal tip of the mesh of clot engaging component 20400 and which runs through the shafts 20200, 20300 to the handle 20100.

As shown in FIGS. 21A-B and 22A-C, in accordance with at least some embodiments of an intraluminal device 20000 in accordance with the present disclosure, the clot engaging component 20400 of intraluminal device 20000 may include a clot anchoring segment 21600 distal to a clot engaging mesh 21400, configured to engage hard clots 21800. The clot anchoring segment 21600 may be manually adjustable and/or self-expandable. In some embodiments, clot anchoring segment 21600 may be heat-treated such that it is configured to expand radially outward when released from catheter 21700. According to various embodiments in which clot anchoring segment 21600 is manually adjustable, its expansion may be controlled, at least in part, by a control wire. In some embodiments, the distal end of a control wire 21550 may be connected to a portion of clot anchoring segment 21600, such as the distal portion thereof. In some embodiments, proximal clot engaging mesh 21400 and clot anchoring segment 21600 may be a unitary structure or may be connected together, such that a force (e.g. a pulling force) exerted upon clot anchoring segment 21600 by the control wire 21550 may transfer to clot engaging mesh 21400, causing simultaneous adjustment of clot anchoring segment 21600 and proximal clot engaging mesh 21400. According to various embodiments in which clot anchoring segment 21600 is self-expanding, a control wire 21500 may be connected to a portion of proximal clot engaging mesh 21400, such as the distal end thereof.

In accordance with alternative embodiments, the intraluminal device may have two or more control wires which run through the shafts 20200, 20300 and which may be connected to a handle 20100. A first control wire 21500 may be connected to proximal clot engaging mesh 21400, such as the distal end thereof, and may be actuated to control expansion of proximal clot engaging mesh 21400. A second control wire 21550 may be connected to a portion of clot anchoring segment 21600, such as a distal end thereof, and may be actuated to control expansion of clot anchoring segment 21600.

Figure 22A:
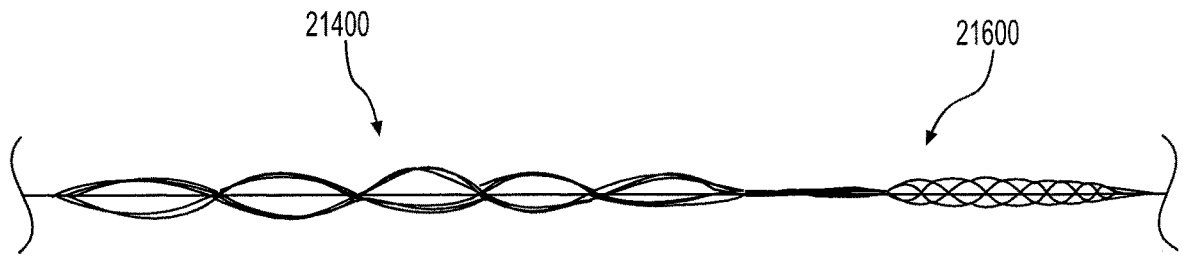
FIG. 22A is an illustration of another exemplary intraluminal device in a first exemplary position in accordance with at least one of the disclosed embodiments.
Figure 22B:
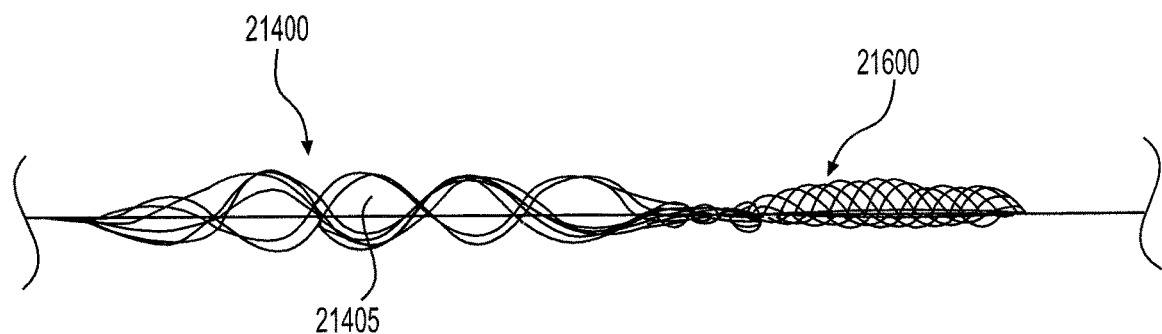
FIG. 22B is an illustration of the exemplary intraluminal device shown in FIG. 22A in a second exemplary position.
Figure 22C:
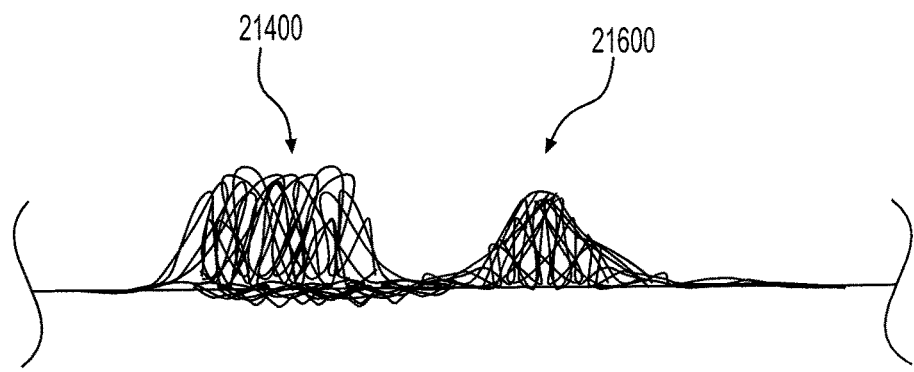
FIG. 22C is an illustration of the exemplary intraluminal device shown in FIG. 22A in a third exemplary position.

In accordance with at least some embodiments of the present disclosure, the outer diameter of proximal clot engaging mesh 21400 may be equal to or larger than the outer diameter of clot anchoring segment 21600 when they are in their respective retracted states. For example, FIG. 22A illustrates an embodiment in which proximal clot engaging mesh 21400 and clot anchoring segment 21600 are both retracted. Additionally or alternatively, the outer diameter of proximal clot engaging mesh 21400 may be equal to or larger than the outer diameter of clot anchoring segment 21600 when they are in their respective fully-expanded states. For example, FIG. 22C illustrates an embodiment in which proximal clot engaging mesh 21400 and clot anchoring segment 21600 are both fully expanded. As explained above, proximal clot engaging mesh 21400 may be configured for expansion independent of clot anchoring segment 21600, and vice versa. For example, FIG. 22B illustrated an embodiment in which proximal clot engaging mesh 21400 is expanded while clot anchoring segment 21600 remains retracted. Proximal clot engaging mesh 21400 may include at least one pore 21405 which is larger than other openings in the intraluminal device, including pores of clot anchoring segment 21600. The at least one pore 21405 may form a clot capturing area, allowing capture of clots within proximal clot engaging mesh 21400. In various embodiments, proximal clot engaging mesh 21400 may be configured for at least partial penetration of a clot and for expansion within the clot, either via a self-expansion mechanism or by actuation of at least one control cable. Proximal clot engaging mesh 21400 may exert an outward radial force upon the clot, achieving fracture and/or capture of the clot.

Figure 21A:
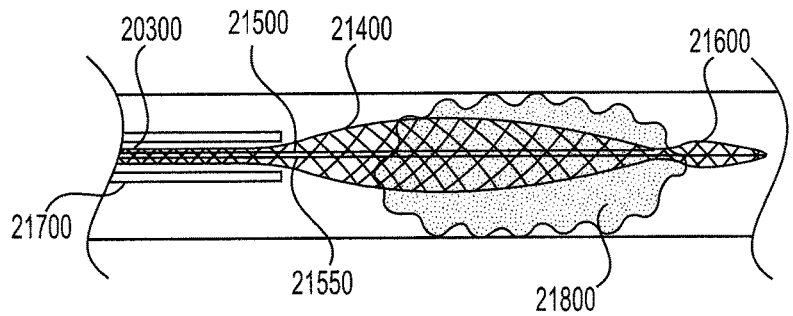
FIG. 21A is an illustration of another exemplary intraluminal device in accordance with at least one of the disclosed embodiments.
Figure 21B:
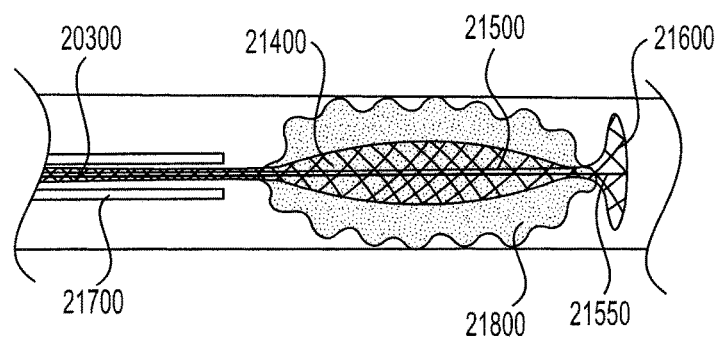
FIG. 21B is an illustration of the exemplary intraluminal device shown in FIG. 21A in an expanded position.

According to various embodiments, the distal end of intraluminal device 20000 may be configured to penetrate a clot. As illustrated in FIGS. 21A-B, proximal clot engaging mesh 21400 and clot anchoring segment 21600 may be pushed through clot 21800 until clot anchoring segment 21600 passes through the distal end of clot 21800 and is positioned within the portion of the vessel distal to the clot 21800. Proximal clot engaging mesh 21400 and clot anchoring segment 21600 may be configured to achieve small respective outer diameters when in their retracted states, such that they may penetrate and pass through clot 21800, such as by manipulation of handle 20100. Proximal clot engaging mesh 21400 may be expanded to capture the clot 21800. However, according to embodiments in which clot 21800 is too rigid for expansion of proximal clot engaging mesh 21400, clot anchoring segment 21600 may be expanded since it is positioned distal to the clot. According to some embodiments, the outer diameter of expanded clot anchoring segment 21600 may be smaller than the inner diameter of the blood vessel, such that clot anchoring segment 21600 does not contact the vessel wall. Alternatively, clot anchoring segment 21600 may be configured to expand until it contacts and conforms to the shape of the vessel wall. Expansion of clot anchoring segment 21600 may form a platform which may trap clot 21800 and prevent it from traveling distal to clot anchoring segment 21600. Once the intraluminal device 20000 is pulled proximally, clot anchoring segment 21600 may engage the clot 21800 and push it upstream. Any adhesion between the clot 21800 and the vessel may be overcome by the resultant shear forces. In some embodiments, partial expansion of proximal clot engaging mesh 21400 within clot 21800 may at least partially secure clot 21800 to proximal clot engaging mesh 21400. Once the clot is pushed proximally by clot anchoring segment 21600 and disengages from the vessel wall, the clot 21800 may be retrieved into the guiding catheter 21700. In some embodiments, at least one of proximal clot engaging mesh 21400 and clot anchoring segment 21600 may remain expanded until the clot 21800 is captured within catheter 21700.

As depicted in FIGS. 23A-B, 24, and 25, in accordance with at least some alternative embodiments of an intraluminal device 20000 in accordance with the present disclosure, the intraluminal device 20000 may include at least one clot anchoring segment and an expandable clot engaging mesh segment 23400 at the distal end thereof. The embodiment depicted in FIGS. 23A-B, 24, and 25 include three clot anchoring segments 23600, 23602, 23604. However, intraluminal device 20000 may include one, two, three, four, five, or more anchoring segments according to various embodiments. Clot engaging mesh segment 23400 may be manually expandable, such as by actuation of control wire 23550, and/or self-expanding, according to mechanisms discussed above, and may be configured to engage hard clots. According to some embodiments, clot anchoring segments 23600-23604 may be expanded by a single control wire 23500 that is connected to the most distal end of these segments, such as the distal-most segment 23604. Alternatively, each clot anchoring segment 23600, 23602, 23604 may be controlled by a respective control wire, which may be connected to the distal end of its respective clot anchoring segment. The respective outer diameters of clot anchoring segments 23600-23604 may be substantially equal in when the retracted state. When in the retracted state, the outer diameter of clot engaging mesh segment 23400 may be equal to or larger than the outer diameter of at least one of clot anchoring segments 23600-23604 when in the retracted state.

Figure 23A:
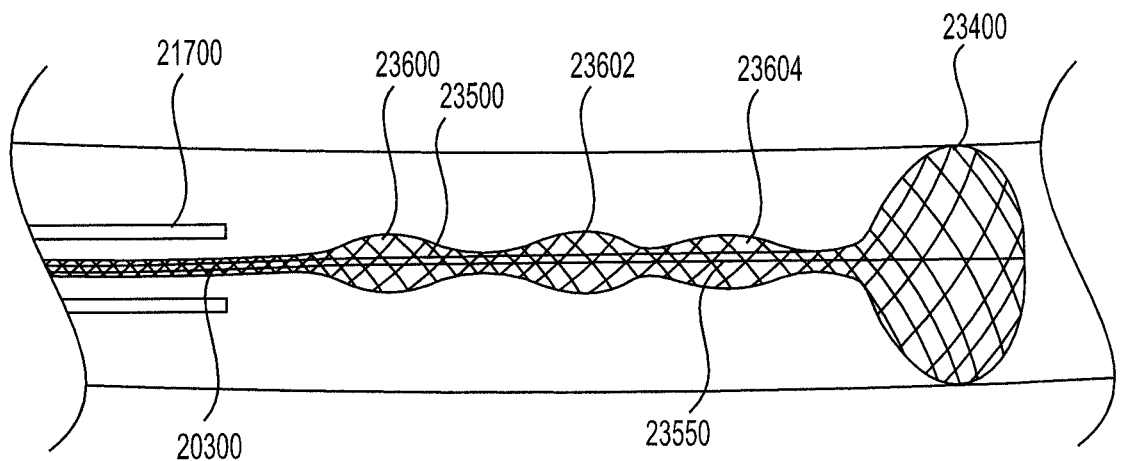
FIG. 23A is an illustration of another exemplary intraluminal device in accordance with at least one of the disclosed embodiments.
Figure 23B:
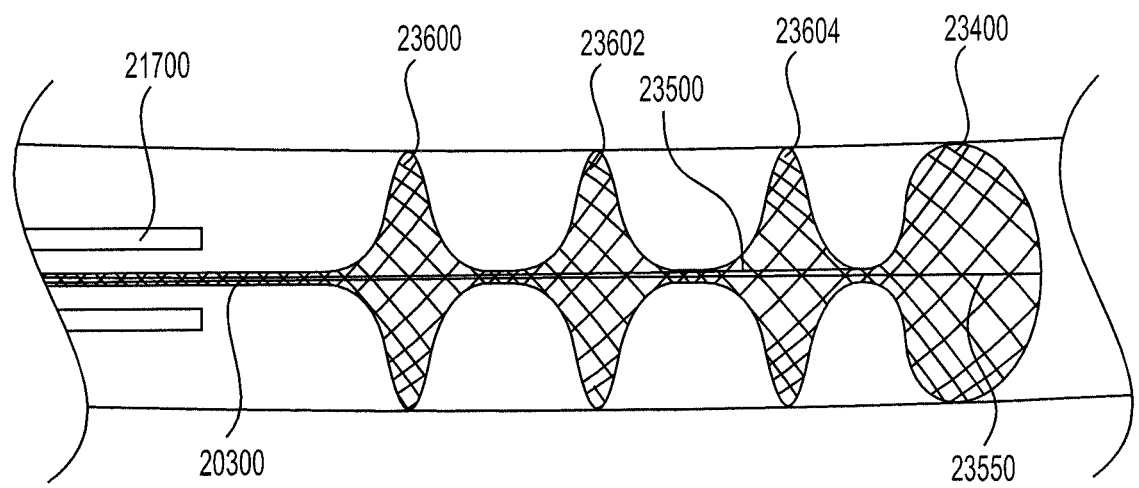
FIG. 23B is an illustration of the exemplary intraluminal device shown in FIG. 23A in an expanded position.
Figure 24:
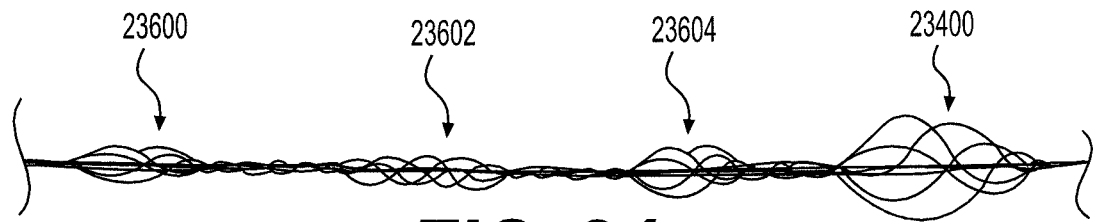
FIG. 24 is an illustration of another exemplary intraluminal device in accordance with at least one of the disclosed embodiments.
Figure 25:
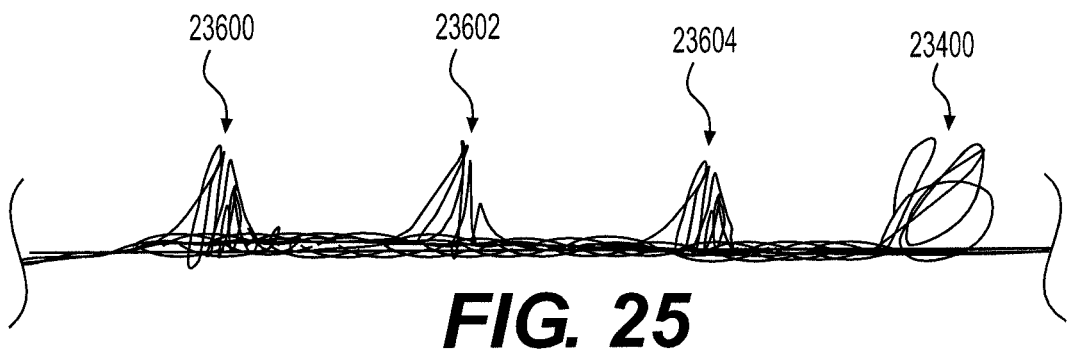
FIG. 25 is an illustration of another exemplary intraluminal device in accordance with at least one of the disclosed embodiments.

As illustrated in FIG. 23B, the clot anchoring segments 23600-23604 may be expanded with high radial forces, each forming a platform configured to substantially prevent passage of clots thereby. According to some embodiments, the outer diameters of expanded clot anchoring segments 23600-23604 may be substantially equal and smaller than the inner diameter of the blood vessel, such that the clot anchoring segments 23600-23604 do not contact the vessel wall. According to alternative embodiments, clot anchoring segments 23600-23604 may be configured to expand until each contacts and conforms to the shape of the vessel wall. In still further embodiments, clot anchoring segments 23600-23604 may be configured for varying outer diameters when fully expanded. In some embodiments, proximal-most segment 23600 may have the largest expanded outer diameter and distal-most segment 23604 may have the smallest expanded outer diameter. In other embodiments, proximal-most segment 23600 may have the smallest expanded outer diameter and distal-most segment 23604 may have the largest expanded outer diameter. In still further embodiments, one or two of segments 23600-23604 may have expanded outer diameters which do not contact the vessel wall, while the remaining segments are configured to expand until they contact and conform with the vessel wall. Clot engaging mesh segment 23400 may be configured to have an outer expanded diameter which is equal to or larger than the expanded outer diameters of clot anchoring segments 23600-23604. Clot engaging mesh segment 23400 may be configured to self-expand independently of clot anchoring segments 23600-23604. For example, FIG. 24 illustrates an embodiment in which clot anchoring segments 23600-23604 are retracted and clot engaging mesh segment 23400 is expanded. while FIG. 25 illustrates an embodiment in which clot anchoring segments 23600-23604 and clot engaging mesh segment 23400 are all expanded.

When expanded, clot anchoring segments 23600-23604 may each form a platform with a larger outer diameter than that of any adjoining section between clot anchoring segments. For example, the transition between clot anchoring segment and adjoining section may be steep so as to form a shelf or seat capable of seating against a portion of a clot. The clot may be trapped between adjacent platforms, and then pushed (or pulled) as the device is retrieved proximally. As shown in FIGS. 23A-B, the clot engaging mesh segment 23400 (which can function as a distal self-expanding filter) may be configured to catch any detached clot fragments to secure a clean pass.

According to some embodiments, the intraluminal device may be delivered into a blood vessel, in proximity to a blood clot. Clot anchoring segments 23600-23604 and clot engaging mesh segment 23400 may be in their retracted states during delivery. The intraluminal device may be positioned such that clot engaging mesh segment 23400 is positioned distal to the clot location, with the clot positioned distal to at least one of clot anchoring segments 23600-23604. In some embodiments, the clot may be positioned proximal to proximal-most clot anchoring segment 23600. Additionally or alternatively, the clot may be positioned between two consecutive clot anchoring segments. Clot engaging mesh segment 23400 may self-expand or be expanded manually to catch any clot fragments distal to the clot anchoring segments. Before, during, or after expansion of clot engaging mesh segment 23400, the clot anchoring segments 23600-23604 may be expanded, either simultaneously or individually. In some embodiments, distal clot anchoring segment 23604 may be expanded first and proximal clot anchoring segment 23600 may be expanded last. Alternatively, in some embodiments, proximal clot anchoring segment 23600 may be expanded first and distal clot anchoring segment 23604 may be expanded last. Expansion of the clot anchoring segments 23600-23604 may form platforms which may trap the clot. The intraluminal device may be pulled proximally, causing the clot anchoring segments to push the clot proximally and into guiding catheter 21700. In some embodiments, at least one of clot anchoring segments 23600-23604 and clot engaging mesh segment 23400 may remain expanded until the clot is captured and removed from the vessel.

Figure 26A:
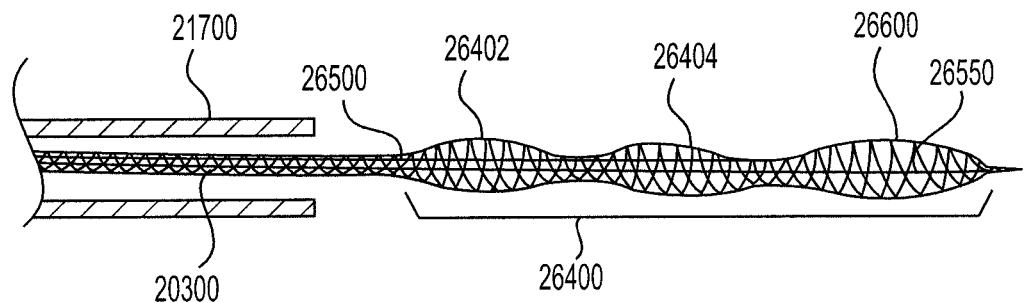
FIG. 26A is an illustration of another exemplary intraluminal device in accordance with at least one of the disclosed embodiments.
Figure 26B:
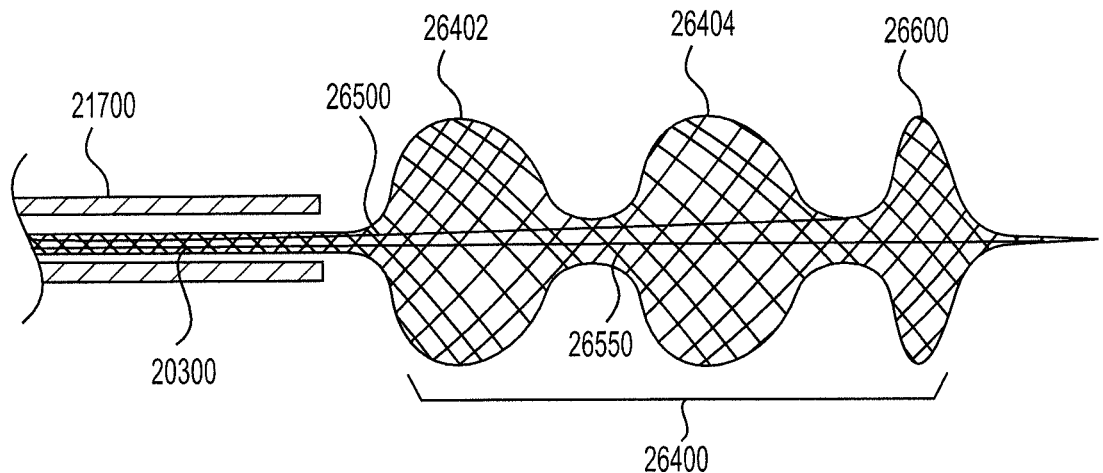
FIG. 26B is an illustration of the exemplary intraluminal device shown in FIG. 26A in an expanded position.

As depicted in FIGS. 26A-B, in accordance with another embodiment, the intraluminal device 20000 may include a long clot engaging segment 26400. The long clot engaging segment 26400 may include several sequential adjustable clot engaging mesh segments 26402 and 26404 to allow improved clot engagement where the clot has mixed hard and soft areas. In some embodiments, long clot engaging segment 26400 may include two, three, four five, or more adjustable clot engaging mesh segments. The clot engaging mesh segments 26402, 26404 can vary in radial force, wire arrangement, diameter, pore size, sparse and design. As a result, the clot engaging mesh segments 26402, 26404 may assume different sizes and/or shapes when expanded and may be configured to exert varying radial outward forces when expanded. The variation in force may be due, at least in part, to the wire arrangement (such as the braiding pattern), the pore size, and the segment length. In one embodiment, a first one of the clot engaging mesh segments 26402, 26404 may be expanded within a clot location. In the event that the segment exerts insufficient force to engage the clot, the first segment may be retracted, the device repositioned, and a second, more rigid clot engaging mesh segment may be expanded to penetrate and capture the clot. In another embodiment, when a first clot engaging mesh segment exerts insufficient outward force to expand and engage a clot, at least one other clot engaging mesh segment may be expanded to engage the clot in a softer area.

As also illustrated in FIGS. 26A-B, in accordance with at least some embodiments of an intraluminal device 20000 in accordance with the present disclosure, at least one distal adjustable clot anchor 26600 may be arranged at the distal end of the intraluminal device. Clot anchor 26600 may be configured to expand with high radial force, forming a platform at the distal end of the device. For example, clot anchor 26600 may be configured to expand until it contacts and conforms with the vessel wall. Once the intraluminal device is pulled proximally, the expanded clot anchor 26600 may engage the clot and push it proximally, in case that the clot engaging mesh segments 26402, 26404 did not capture the clot or a portion thereof. In some embodiments, at least one of clot engaging mesh segments 26402, 26404 and adjustable clot anchor 26600 may remain expanded until the clot is captured and removed from the vessel. Furthermore, a control wire 26550 may be attached to the distal-most anchoring segment 26600, and/or one or more control wires (such as control wire 26500) may be attached to the distal portion of one or more clot engaging mesh segments 26402 and 26404. Such control wires may be actuated to expand and retract their respective segment(s) as discussed throughout.

Figure 27:
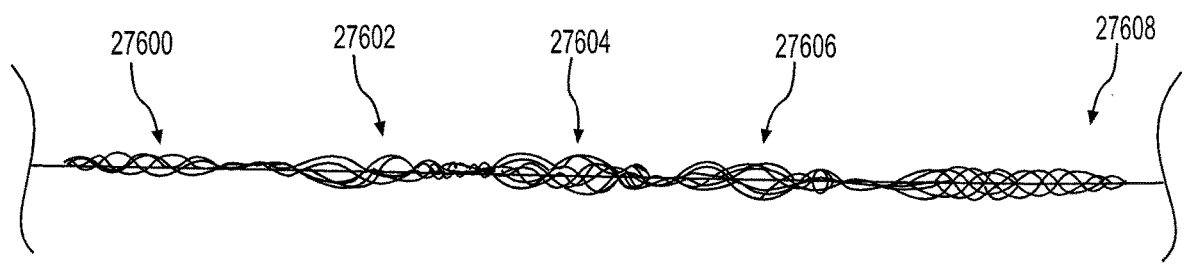
FIG. 27 is an illustration of another exemplary intraluminal device in accordance with at least one of the disclosed embodiments.
Figure 28:
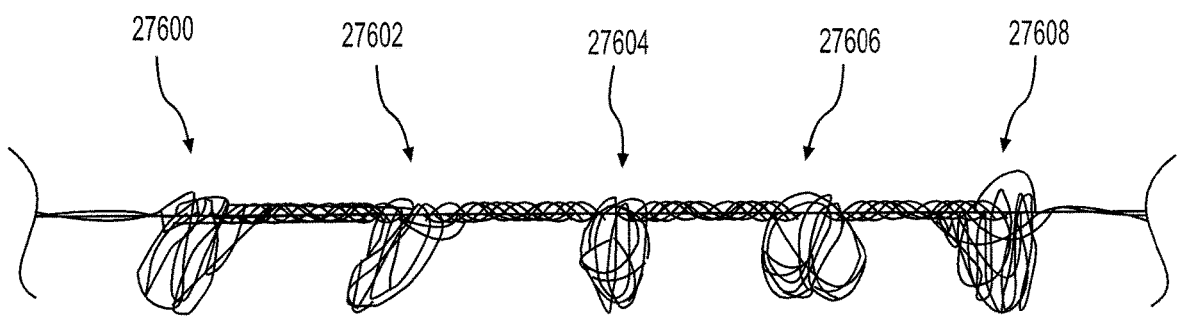
FIG. 28 is an illustration of another exemplary intraluminal device in accordance with at least one of the disclosed embodiments.

As depicted in FIGS. 27-28, in accordance with another embodiment, the intraluminal device 20000 may include several adjustable clot anchoring segments 27600-27608, each of which may be configured to change its respective configuration to consequent platforms when expanded, to allow clot entrapment between the platforms. The intraluminal device may include two, three, four, five, six, seven, eight, nine, ten, or more clot anchoring segments. The clot anchoring segments 27600-27608 may vary in radial force, wire arrangement, diameter, pore size, sparse and design, for example. In some embodiments, each clot anchoring segment 27600-27608 may include a respective control wire, such that the segments may be individually expanded. In other embodiments, a single or multiple control wires may be attached to the distal-most clot anchoring segment and may be actuated to simultaneously expand all clot anchoring segments 27600-27608. In one embodiment, a first one of the clot anchoring segments 27600-27608 may be expanded distal to a clot location, so as to capture the clot. In the event that the clot anchoring segment does not capture the clot or at least a fragment thereof, a second clot anchoring segment may be expanded, for example distal to the first clot anchoring segment, to capture the remaining fragments of the clot. In some embodiments, the second clot anchoring segment may have a larger expanded outer diameter than the first clot anchoring segment and/or exert greater outward force than the first clot anchoring segment when expanded. For example, the second clot anchoring segment may be configured to expand until it contacts and conforms to the shape of the vessel wall. Advantageously, this may permit any clot fragments not captured by the first clot anchoring segment to be captured by the second clot anchoring segment. According to other embodiments, two or more of clot anchoring segments 27600-27608 may be expanded simultaneously, thus capturing the clot and any fragments thereof. Once the device is pulled proximally, the platforms formed by clot anchoring segments 27600-27608 may engage the clot and any fragments thereof and push it proximally. The platforms may also act as a filter, catching detached clot fragments. In some embodiments, at least one of clot anchoring segments 27600-27608 may remain expanded until the clot is captured and removed from the vessel.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods can be modified in any manner, including by reordering steps or inserting or deleting steps. It is intended, therefore, that the specification and examples be considered as example only, with a true scope and spirit being indicated by the following claims and their full scope of equivalents.

What is claimed is:

1. An intraluminal device including an elongated structure formed of a plurality of wires extending from the proximal end of the elongated structure to the distal end of the elongated structure, the intraluminal device comprising:
   a first region of the elongated structure, wherein the plurality of wires is twisted within the first region to form a shaft;
   a second region of the elongated structure adjacent to the first region of the elongated structure, wherein the plurality of wires is woven within the second region to form a scaffold;
   a third region of the elongated structure situated distally from the second region of the elongated structure, the third region including a plurality of sets of looped wires that cooperate with each other to form a clot capturing area, each of the plurality of sets of looped wires comprising two or more loosely looped or loosely coupled wires from the plurality of wires, wherein the clot capturing area includes at least two strand configurations or at least two braiding configurations; and
   a fourth region located distally from the third region of the elongated structure, the fourth region including a distal filter woven from the plurality of sets of looped wires,
   wherein at least one set of looped wires cooperates with at least one other set of looped wires in the third region of the elongated structure to form at least one expandable mesh segment configured to engage an obstruction within a body lumen,
   wherein a first set of looped wires intertwines with a second set of looped wires within the third region to define a junction structure, the junction structure including a weaving of the first set of looped wires and the second set of looped wires such that a first wire of the first set of looped wires is situated between two wires of the second set of looped wires and a second wire of the second set of looped wires is situated between two wires of the first set of looped wires,
   wherein the junction structure is configured such that when an opening force is exerted on the elongated structure, the junction structure provides structural support to maintain a strand configuration of one or more of the first set of looped wires and the second set of looped wires, wherein the scaffold in the second region of the elongated structure is configured to support openings between the sets of looped wires in the at least one expandable mesh segment, and wherein the plurality of wires is arranged to form at least one clot anchoring segment in the fourth region of the elongated structure, the at least one clot anchoring segment configured to trap the obstruction to prevent downstream movement of the obstruction relative to the elongated structure.

2. The intraluminal device of claim 1, wherein the at least one clot anchoring segment is configured to radially expand into a platform formed of the plurality of wires, the platform having a larger outer diameter than at least one portion of the elongated structure that is adjacent to the platform.

3. The intraluminal device of claim 1, wherein the at least one clot anchoring segment is configured to be self-expandable.

4. The intraluminal device of claim 1, further comprising:
a first control wire and a second control wire, wherein the first control wire is configured to control expansion of the at least one expandable mesh segment and the second control wire is configured to control expansion of the at least one clot anchoring segment.

5. The intraluminal device of claim 1, wherein the at least one expandable mesh segment includes at least one pore between the sets of looped wires, the at least one pore being larger than openings formed between the plurality of wires in the first region, second region, and fourth region of the elongated structure.

6. The intraluminal device of claim 2, wherein the at least one clot anchoring segment is configured to radially expand into the platform at a location downstream of the obstruction and is configured to trap the obstruction and push the obstruction in an upstream direction.

7. The intraluminal device of claim 1, wherein the at least one clot anchoring segment includes two adjustable clot anchoring segments.

8. The intraluminal device of claim 7, wherein the two adjustable clot anchoring segments are configured to be radially expanded by a single control wire that is connected to a distal end of the distal-most clot anchoring segment of the two adjustable clot anchoring segments.

9. The intraluminal device of claim 7, wherein the two adjustable clot anchoring segments are configured to be radially expanded by separate control wires.

10. The intraluminal device of claim 1, wherein the at least one expandable mesh segment includes two adjustable mesh segments that are separated by a portion of the third region of the elongated structure that is configured to have a smaller outer diameter than the two adjustable mesh segments.

11. The intraluminal device of claim 10, wherein the two adjustable mesh segments are configured to pass through at least one obstruction within the body lumen and to expand within the at least one obstruction.

12. The intraluminal device of claim 2, wherein the platform is configured to contact a vessel wall of the body lumen when the at least one clot anchoring segment is radially-expanded.

13. The intraluminal device of claim 1, wherein the at least one clot anchoring segment and the at least one expandable mesh segment are configured to be radially expanded by a single control wire.

14. The intraluminal device of claim 1, wherein the at least one expandable mesh segment is configured to be radially expanded by a control wire that is connected to a distal end of the at least one expandable mesh segment.

15. The intraluminal device of claim 1, wherein the at least one expandable mesh segment is configured to pass through the obstruction and to expand within the obstruction to penetrate and contain the obstruction.

16. The intraluminal device of claim 10, wherein the plurality of wires has different wire braiding patterns within the two adjustable mesh segments such that the two adjustable mesh segments are configured to exert outward radial forces of different magnitudes when the two adjustable mesh segments expand within at least one obstruction within the body lumen.

17. The intraluminal device of claim 1, the intraluminal device further comprising a transition region situated between the third region and the fourth region, wherein a diameter of the transition region is smaller than both a diameter of the third region and a diameter of the fourth region, and wherein the at least one clot anchoring segment of the fourth region is configured to radially expand into a platform formed of the plurality of wires.

18. The intraluminal device of claim 1, the intraluminal device further comprising a plurality of transition regions, wherein the at least one clot anchoring segment includes a plurality of clot anchoring segments, each clot anchoring segment including a platform and each transition region being situated proximal to each clot anchoring segment, and wherein a diameter of each transition region is smaller than a diameter of each platform.

19. The intraluminal device of claim 1, wherein the at least one clot anchoring segment includes a plurality of clot anchoring segments configured to radially expand into a plurality of platforms formed of the plurality of wires, each platform having a different diameter.

* * * * *